(12) United States Patent
Bottini et al.

(10) Patent No.: US 10,604,585 B2
(45) Date of Patent: Mar. 31, 2020

(54) MODULATION OF PTPRA TO TREAT ARTHRITIS

(71) Applicants: La Jolla Institute for Allergy & Immunology, La Jolla, CA (US); The Regents of the University of California, Oakland, CA (US)

(72) Inventors: Nunzio Bottini, San Diego, CA (US); Gary Firestein, Del Mar, CA (US); Stephanie Stanford, La Jolla, CA (US)

(73) Assignees: La Jolla Institute for Allergy & Immunology, La Jolla, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/509,829

(22) PCT Filed: Sep. 9, 2015

(86) PCT No.: PCT/US2015/049228
§ 371 (c)(1),
(2) Date: Mar. 8, 2017

(87) PCT Pub. No.: WO2016/040510
PCT Pub. Date: Mar. 17, 2016

(65) Prior Publication Data
US 2017/0247469 A1    Aug. 31, 2017

Related U.S. Application Data

(60) Provisional application No. 62/048,129, filed on Sep. 9, 2014.

(51) Int. Cl.
| | |
|---|---|
| *A61K 48/00* | (2006.01) |
| *C07H 21/02* | (2006.01) |
| *C07H 21/04* | (2006.01) |
| *C07K 16/40* | (2006.01) |
| *C12N 15/113* | (2010.01) |
| *G01N 33/50* | (2006.01) |

(52) U.S. Cl.
CPC .......... *C07K 16/40* (2013.01); *C12N 15/1138* (2013.01); *C12Y 301/03048* (2013.01); *G01N 33/502* (2013.01); *C07K 2317/76* (2013.01); *C12N 2310/11* (2013.01); *C12N 2310/314* (2013.01); *C12N 2310/3233* (2013.01); *C12N 2310/351* (2013.01); *G01N 2333/912* (2013.01); *G01N 2440/14* (2013.01)

(58) Field of Classification Search
CPC .......................... A61K 31/713; C12N 15/113
See application file for complete search history.

(56) References Cited

U.S. PATENT DOCUMENTS

| | | | | |
|---|---|---|---|---|
| 2004/0023904 | A1* | 2/2004 | Cowsert | C12N 15/1137 514/44 A |
| 2007/0231791 | A1 | 10/2007 | Olsen et al. | |
| 2010/0022619 | A1 | 1/2010 | Bhanot et al. | |
| 2010/0121253 | A1* | 5/2010 | Sen | C12N 15/87 514/1.1 |
| 2013/0171164 | A1* | 7/2013 | Bottini | A61K 31/7088 424/158.1 |
| 2013/0330312 | A1* | 12/2013 | Greene | A61K 38/53 424/94.3 |

OTHER PUBLICATIONS

Aschner, Y. et al. (May 2014, e-published Mar. 17, 2014). "Protein tyrosine phosphatase α mediates profibrotic signaling in lung fibroblasts through TGF-β responsiveness," *Am J Pathol* 184(5):1489-1502.
Bodrikov, V. et al. (Jan. 3, 2005, e-published Dec. 28, 2004). "RPTPα is essential for NCAM-mediated p59fyn activation and neurite elongation," *J Cell Biol* 168(1):127-139.
Bottini, N. et al. (Jan. 2013, e-published Nov. 13, 2012). "Duality of fibroblast-like synoviocytes in RA: passive responders and imprinted aggressors," *Nat Rev Rheumatol* 9(1):24-33.
Chen, M. et al. (Apr. 28, 2006, e-published Feb. 28, 2006). "Integrin-induced tyrosine phosphorylation of protein-tyrosine phosphatase-alpha is required for cytoskeletal reorganization and cell migration," *J Biol Chem* 281(17):11972-11980.
International Search Report dated Dec. 18, 2015, for PCT Application No. PCT/US2015/049228, filed Sep. 9, 2015, 5 pages.
Lee, E.Y. et al. (Mar. 2013, e-published Oct. 22, 2012). "The interaction between CXCL10 and cytokines in chronic inflammatory arthritis," *Autoimmun Rev* 12(5):554-557.
Monach, P.A. et al. (May 2008). "The K/BxN arthritis model," *Curr Protoc Immunol*, Chapter 15: Unit 15.22.
Rajshankar, D. et al. (Aug. 5, 2013). "Role of PTPα in the destruction of periodontal connective tissues," *PLoS One* 8(8):e70659.
Stanford, S.M. et al. (May 2013). "Protein tyrosine phosphatase expression profile of rheumatoid arthritis fibroblast-like synoviocytes: a novel role of SH2 domain-containing phosphatase 2 as a modulator of invasion and survival," *Arthritis Rheum* 65(5):1171-1180.
Stanford, S.M. et al. (Jan. 2016, e-published Nov. 6, 2014). "TGFβ responsive tyrosine phosphatase promotes rheumatoid synovial fibroblast invasiveness," *Ann Rheum Dis* 75(1):295-302.
Written Opinion dated Dec. 18, 2015, for PCT Application No. PCT/US2015/049228, filed Sep. 9, 2015, 10 pages.

* cited by examiner

*Primary Examiner* — Amy H Bowman
(74) *Attorney, Agent, or Firm* — Mintz, Levin, Cohn, Ferris, Glovsky and Popeo, P.C.

(57) ABSTRACT

Presented is a method for treating inflammation and autoimmune diseases through the use of a phosphatase rheumatoid arthritis (PT-PRA) antagonist.

11 Claims, 12 Drawing Sheets
Specification includes a Sequence Listing.

Arthritis Mouse Ankles
IHC:
anti-RPTPα

WT

KO

RA Synovium
IHC:
anti-RPTPα

SEQUENCE LISTING

<160> NUMBER OF SEQ ID NOS: 5

<210> SEQ ID NO 1
<211> LENGTH: 3637
<212> TYPE: DNA
<213> ORGANISM: Homo sapiens

<400> SEQUENCE: 1

| | | | | | |
|---|---|---|---|---|---|
| cacgctcagg | ggagcaggta | ccccttctcc | taaagatgaa | gaggagcaaa | ctggcactaa | 60 |
| gcaaggccat | cgagagcggg | gacactgacc | tggtgttcac | ggtgttgctg | cacctgaaga | 120 |
| acgagctgaa | ccgaggagat | tttttcatga | cccttcggaa | tcagcccatg | gccctcagtt | 180 |
| tgtaccgaca | gttctgtaag | catcaggagc | tagagacgct | gaaggacctt | tacaatcagg | 240 |
| atgacaatca | ccaggaattg | gcagcttcc | acatccgagc | cagctatgct | gcagaagagc | 300 |
| gtattgaggg | gcgagtagca | gctctgcaga | cagccgccga | tgccttctac | aaggccaaga | 360 |
| atgagtttgc | agccaaggct | acagaggatc | aaatgcggct | cctacggctg | cagcggcgcc | 420 |
| tagaagacga | gctgggggc | cagttcctag | acctgtctct | acatgacaca | gttaccaccc | 480 |
| tcattcttgg | cggtcacaac | aagcgtgcag | agcagctggc | acgtgacttc | cgcatccctg | 540 |
| acaagaggtg | acacaactaa | aaaaaaacaa | aggtatttat | ggaattccac | tgagtggtaa | 600 |
| tggatgatgc | agttcaaata | actaaggaca | catgttcaaa | gagcataatt | aacttttaa | 660 |
| aagaagctaa | taagcatgga | ttcctggttc | attcttgttc | tgctcggcag | tggtctgata | 720 |
| tgtgtcagtg | ccaacaatgc | taccacagtt | gcaccttctg | taggaattac | aagattaatt | 780 |
| aactcatcaa | cggcagaacc | agttaaagaa | gaggccaaaa | cttcaaatcc | aacttcttca | 840 |
| ctaacttctc | tttctgtggc | accaacattc | agcccaaata | taactctggg | acccaccctat | 900 |
| ttaaccactg | tcaattcttc | agactctgac | aatgggacca | caagaacagc | aagcaccaat | 960 |
| tctataggca | ttacaatttc | accaaatgga | acgtggcttc | cagataacca | gttcacggat | 1020 |
| gccagaacag | aaccctggga | ggggaattcc | agcaccgcag | caaccactcc | agaaactttc | 1080 |
| cctccttcag | gtaattctga | ctcgaaggac | agaagagatg | agacaccaat | tattgcggtg | 1140 |
| atggtggccc | tgtcctctct | gctagtgatc | gtgtttatta | tcatagttt | gtacatgtta | 1200 |
| aggtttaaga | atacaagca | agctgggagc | cattccaatt | cttccgctt | atccaacggc | 1260 |
| cgcactgagg | atgtggagcc | ccagagtgtg | ccacttctgg | ccagatcccc | aagcaccaac | 1320 |
| aggaaatacc | caccccctgcc | cgtggacaag | ctggaagagg | aaattaaccg | gagaatggca | 1380 |
| gacgacaata | agctcttcag | ggaggaattc | aacgctctcc | ctgcatgtcc | tatccaggcc | 1440 |
| acctgtgagg | ctgcttccaa | ggaggaaaac | aaggaaaaaa | atcgatatgt | aaacatcttg | 1500 |
| ccttatgacc | actctagagt | ccacctgaca | ccggttgaag | gggttccaga | ttctgattac | 1560 |
| atcaatgctt | cattcatcaa | cggctaccaa | gaaaagaaca | aattcattgc | tgcacaagga | 1620 |
| ccaaaagaag | aaacggtgaa | tgatttctgg | cggatgatct | gggaacaaaa | cacagccacc | 1680 |
| atcgtcatgg | ttaccaacct | gaaggagaga | aaggagtgca | agtgcgccca | gtactggcca | 1740 |
| gaccaaggct | gctggaccta | tgggaatatt | cgggtgtctg | tagaggatgt | gactgtcctg | 1800 |
| gtggactaca | cagtacgaa | gttctgcatc | cagcaggtgg | gcgacatgac | caacagaaag | 1860 |
| ccacagcgcc | tcatcactca | gttccactttt | accagctggc | cagactttgg | ggtgcctttt | 1920 |
| accccgatcg | gcatgctcaa | gttcctcaag | aaggtgaagg | cctgtaaccc | tcagtatgca | 1980 |
| ggggccatcg | tggtccactg | cagtgcaggt | gtagggcgta | caggtacctt | tgtcgtcatt | 2040 |
| gatgccatgc | tggacatgat | gcatacagaa | cggaaggtgg | acgtgtatgg | ctttgtgagc | 2100 |

```
cggatccggg cacagcgctg ccagatggtg caaaccgata tgcagtatgt cttcatatac    2160
caagcccttc tggagcatta tctctatgga gatacagaac tggaagtgac ctctctagaa    2220
acccacctgc agaaaattta caacaaaatc ccagggacca gcaacaatgg attagaggag    2280
gagtttaaga agttaacatc aatcaaaatc cagaatgaca agatgcggac tggaaacctt    2340
ccagccaaca tgaagaagaa ccgtgtttta cagatcattc catatgaatt caacagagtg    2400
atcattccag ttaagcgggg cgaagagaat acagactatg tgaacgcatc ctttattgat    2460
ggctaccggc agaaggactc ctatatcgcc agccagggcc ctcttctcca cacaattgag    2520
gacttctggc aatgatctg ggagtggaaa tcctgctcta tcgtgatgct aacagaactg    2580
gaggagagag gccaggagaa gtgtgcccag tactggccat ctgatggact ggtgtcctat    2640
ggagatatta cagtggaact gaagaaggag gaggaatgtg agagctacac cgtccgagac    2700
ctcctggtca ccaacaccag ggagaataag agccggcaga tccggcagtt ccacttccat    2760
ggctggcctg aagtgggcat ccccagtgac ggaaagggca tgatcagcat catcgccgcc    2820
gtgcagaagc agcagcagca gtcagggaac cacccccatca ccgtgcactg cagcgccggg    2880
gcaggaagga cggggacctt ctgtgccctg agcaccgtcc tggagcgtgt gaaagcagag    2940
gggattttgg atgtcttcca gactgtcaag agcctgcggc tacagaggcc acacatggtc    3000
cagacactgg aacagtatga gttctgctac aaggtggtgc aggagtatat tgatgcattc    3060
tcagattatg ccaacttcaa gtaagcggca acaagggtcc gtggaccagg aggattgcct    3120
ttaatatttt gtaatattct gttttgttaa tatccccaa attgtgtata tatcttataa    3180
ctgttttaga aattggtaca taggcttcta ttacctatta ggtggaaatt ttatatgtaa    3240
atgtgttagc actgatagtc ctttttccaa tgttttattg gggaattaaa tagtgtgatg    3300
tttggattga tatcgtgaaa tcctcagccg agaaattggg ctggattgtg ctttggttaa    3360
tacatctttc cctaaagaag ataaacacaa aatccattcc aggtagctcg gcaccaacta    3420
agaaaaaaag cacaaagttc tcagagctct cgaggaaagt ggttgtcccc gtaccaccat    3480
gcactgtaaa tatccctccc ctctctcccct ggtcccctcc cccatcccca ccactgatat    3540
catggggagt aataggacca gagcggtatc tctggcacca cactagggac tatcaggtaa    3600
taaaagcttt gactccctga aaaaaaaaaa aaaaaa                              3637
```

<210> SEQ ID NO 2
<211> LENGTH: 3328
<212> TYPE: DNA
<213> ORGANISM: Homo sapiens

<400> SEQUENCE: 2

```
ctgcggcgag tgcggcgctg acagagacgc gcgcgcgcgc gatcgcgctc ggaccccggc     60
cgctgccgcc atcactgtcg cccgcccagt cgcccctcag ccgcttcccc tcgccatgga    120
ggcgaggccg ccgccgccgc cgcggggctc ggagccgcgg gccgggcggc ggccctgagg    180
gctagtggcg gcccgaaacg ccgccgcgga gccgaggcgg agccgctgtc ctcgtcccca    240
gcggtcccgc ccaacgcccg actctgtgac acaactaaaa aaaacaaag gtatttatgg    300 aattccactg agtggtaatg gatgatgcag ttcaaataac taaggacaca tgttcaaaga    360
gcataattaa cttttttaaaa gaagctaata agcatggatt cctggttcat tcttgttctg    420
ctcggcagtg gtctgatatg tgtcagtgcc aacaatgcta ccacagttgc accttctgta    480
ggaattacaa gattaattaa ctcatcaacg gcagaaccag ttaaagaaga ggccaaaact    540
```

```
tcaaatccaa cttcttcact aacttctctt tctgtggcac caacattcag cccaaatata    600
actctgggac ccacctattt aaccactgtc aattcttcag actctgacaa tgggaccaca    660
agaacagcaa gcaccaattc tataggcatt acaatttcac caaatggaac gtggcttcca    720
gataaccagt tcacggatgc cagaacagaa ccctgggagg ggaattccag caccgcagca    780
accactccag aaactttccc tccttcagat gagacaccaa ttattgcggt gatggtggcc    840
ctgtcctctc tgctagtgat cgtgtttatt atcatagttt tgtacatgtt aaggtttaag    900
aaatacaagc aagctgggag ccattccaat tctttccgct tatccaacgg ccgcactgag    960
gatgtggagc cccagagtgt gccacttctg gccagatccc caagcaccaa caggaaatac   1020
ccacccctgc ccgtggacaa gctggaagag gaaattaacc ggagaatggc agacgacaat   1080
aagctcttca gggaggaatt caacgctctc cctgcatgtc ctatccaggc cacctgtgag   1140
gctgcttcca aggaggaaaa caaggaaaaa aatcgatatg taaacatctt gccttatgac   1200
cactctagag tccacctgac accggttgaa ggggttccag attctgatta catcaatgct   1260
tcattcatca acggctacca agaaaagaac aaattcattg ctgcacaagg accaaaagaa   1320
gaaacggtga atgatttctg gcggatgatc tgggaacaaa acacagccac catcgtcatg   1380
gttaccaacc tgaaggagag aaaggagtgc aagtgcgccc agtactggcc agaccaaggc   1440
tgctggacct atgggaatat tcgggtgtct gtagaggatg tgactgtcct ggtggactac   1500
acagtacgga agttctgcat ccagcaggtg ggcgacatga ccaacagaaa gccacagcgc   1560
ctcatcactc agttccactt taccagctgg ccagactttg gggtgccttt taccccgatc   1620
ggcatgctca gttcctcaa gaaggtgaag gcctgtaacc ctcagtatgc aggggccatc   1680
gtggtccact gcagtgcagg tgtagggcgt acaggtacct tgtcgtcat tgatgccatg   1740 ctggacatga tgcatacaga acggaaggtg gacgtgtatg gctttgtgag ccggatccgg   1800
gcacagcgct gccagatggt gcaaaccgat atgcagtatg tcttcatata ccaagccctt   1860
ctggagcatt atctctatgg agatacagaa ctggaagtga cctctctaga aacccacctg   1920
cagaaaattt acaacaaaat cccagggacc agcaacaatg gattagagga ggagtttaag   1980
aagttaacat caatcaaaat ccagaatgac aagatgcgga ctggaaacct tccagccaac   2040
atgaagaaga accgtgtttt acagatcatt ccatatgaat tcaacagagt gatcattcca   2100
gttaagcggg gcgaagagaa tacagactat gtgaacgcat cctttattga tggctaccgg   2160
cagaaggact cctatatcgc cagccagggc cctcttctcc acacaattga ggacttctgg   2220
cgaatgatct gggagtggaa atcctgctct atcgtgatgc taacagaact ggaggagaga   2280
ggccaggaga agtgtgccca gtactggcca tctgatggac tggtgtccta tggagatatt   2340
acagtggaac tgaagaagga ggaggaatgt gagagctaca ccgtccgaga cctcctggtc   2400
accaacacca gggagaataa gagccggcag atccggcagt ccacttcca tggctggcct   2460 gaagtgggca tccccagtga cggaaagggc atgatcagca tcatcgccgc cgtgcagaag   2520
cagcagcagc agtcagggaa ccaccccatc accgtgcact gcagcgccgg ggcaggaagg   2580
acggggacct tctgtgccct gagcaccgtc ctggagcgtg tgaaagcaga ggggattttg   2640
gatgtcttcc agactgtcaa gagcctgcgg ctacagaggc cacacatggt ccagacactg   2700
gaacagtatg agttctgcta caaggtggtg caggagtata ttgatgcatt ctcagattat   2760
gccaacttca gtaagcggc aacaagggtc cgtggaccag gaggattgcc tttaatattt   2820
tgtaatattc tgttttgtta atataccccca aattgtgtat atatcttata actgttttag   2880
aaattggtac ataggcttct attacctatt aggtggaaat tttatatgta aatgtgttag   2940
```

```
cactgatagt cctttttcca atgttttatt ggggaattaa atagtgtgat gtttggattg    3000
atatcgtgaa atcctcagcc gagaaattgg gctggattgt gctttggtta atacatcttt    3060
ccctaaagaa gataaacaca aaatccattc caggtagctc ggcaccaact aagaaaaaaa    3120
gcacaaagtt ctcagagctc tcgaggaaag tggttgtccc cgtaccacca tgcactgtaa    3180
atatccctcc cctctctccc tggtcccctc cccatcccc accactgata tcatggggag    3240
taataggacc agagcggtat ctctggcacc acactaggga ctatcaggta ataaaagctt    3300
tgactccctg aaaaaaaaaa aaaaaaa                                        3328

<210> SEQ ID NO 3
<211> LENGTH: 3153
<212> TYPE: DNA
<213> ORGANISM: Homo sapiens

<400> SEQUENCE: 3
gtgacacaac taaaaaaaaa caaaggtatt tatggaattc cactgagtgg taatggatga      60
tgcagttcaa ataactaagg acacatgttc aaagagcata attaactttt taaaagaagc     120
tagacttctt cagaagcttg ccagtttttc aagctgattt ctctcactgg caactcttca     180
gagtgctgtt cctactccac cctcccctgg tgataagcat ggattcctgg ttcattcttg     240
ttctgctcgg cagtggtctg atatgtgtca gtgccaacaa tgctaccaca gttgcacctt     300
ctgtaggaat tacaagatta attaactcat caacggcaga accagttaaa gaagaggcca     360
aaacttcaaa tccaacttct tcactaactt ctctttctgt ggcaccaaca ttcagcccaa     420
atataactct gggacccacc tatttaacca ctgtcaattc ttcagactct gacaatggga     480
ccacaagaac agcaagcacc aattctatag gcattacaat tcaccaaat ggaacgtggc     540 ttccagataa ccagttcacg gatgccagaa cagaaccctg ggaggggaat tccagcaccg     600
cagcaaccac tccagaaact ttccctcctt cagatgagac accaattatt gcggtgatgg     660
tggccctgtc ctctctgcta gtgatcgtgt ttattatcat agttttgtac atgttaaggt     720
ttaagaaata caagcaagct gggagccatt ccaattcttt ccgcttatcc aacggccgca     780
ctgaggatgt ggagccccag agtgtgccac ttctggccag atcccaagc accaacagga     840 aatacccacc cctgcccgtg gacaagctgg aagaggaaat taccggaga atggcagacg     900 acaataagct cttcagggag gaattcaacg ctctccctgc atgtcctatc caggccacct     960
gtgaggctgc ttccaaggag gaaaacaagg aaaaaatcg atatgtaaac atcttgcctt    1020
atgaccactc tagagtccac ctgacaccgg ttgaaggggg tccagattct gattacatca    1080
atgcttcatt catcaacggc taccaagaaa agaacaaatt cattgctgca caaggaccaa    1140
aagaagaaac ggtgaatgat ttctggcgga tgatctggga acaaaacaca gccaccatcg    1200
tcatggttac caacctgaag gagagaaagg agtgcaagtg cgcccagtac tggccagacc    1260
aaggctgctg gacctatggg aatattcggg tgtctgtaga ggatgtgact gtcctggtgg    1320
actacacagt acggaagttc tgcatccagc aggtgggcga catgaccaac agaaagccac    1380
agcgcctcat cactcagttc cactttacca gctggccaga ctttgggggtg ccttttaccc    1440 cgatcggcat gctcaagttc ctcaagaagg tgaaggcctg taaccctcag tatgcagggg    1500
ccatcgtggt ccactgcagt gcaggtgtag ggcgtacagg tacctttgtc gtcattgatg    1560
ccatgctgga catgatgcat acagaacgga aggtggacgt gtatggcttt gtgagccgga    1620
tccgggcaca gcgctgccag atggtgcaaa ccgatatgca gtatgtcttc atataccaag    1680
```

```
cccttctgga gcattatctc tatggagata cagaactgga agtgacctct ctagaaaccc    1740
acctgcagaa aatttacaac aaaatcccag ggaccagcaa caatggatta gaggaggagt    1800
ttaagaagtt aacatcaatc aaaatccaga atgacaagat gcggactgga aaccttccag    1860
ccaacatgaa gaagaaccgt gttttacaga tcattccata tgaattcaac agagtgatca    1920
ttccagttaa gcggggcgaa gagaatacag actatgtgaa cgcatccttt attgatggct    1980
accggcagaa ggactcctat atcgccagcc agggccctct tctccacaca attgaggact    2040
tctggcgaat gatctgggag tggaaatcct gctctatcgt gatgctaaca gaactggagg    2100
agagaggcca ggagaagtgt gcccagtact ggccatctga tggactggtg tcctatggag    2160
atattacagt ggaactgaag aaggaggagg aatgtgagag ctacaccgtc cgagacctcc    2220
tggtcaccaa caccagggag aataagagcc ggcagatccg gcagttccac ttccatggct    2280
ggcctgaagt gggcatcccc agtgacggaa agggcatgat cagcatcatc gccgccgtgc    2340
agaagcagca gcagcagtca gggaaccacc ccatcaccgt gcactgcagc gccggggcag    2400
gaaggacggg gaccttctgt gccctgagca ccgtcctgga gcgtgtgaaa gcagagggga    2460
ttttggatgt cttccagact gtcaagagcc tgcggctaca gaggccacac atggtccaga    2520
cactggaaca gtatgagttc tgctacaagg tggtgcagga gtatattgat gcattctcag    2580
attatgccaa cttcaagtaa gcggcaacaa gggtccgtgg accaggagga ttgcctttaa    2640
tattttgtaa tattctgttt tgttaatata ccccaaattg tgtatatatc ttataactgt    2700
tttagaaatt ggtacatagg cttctattac ctattaggtg gaaattttat atgtaaatgt    2760
gttagcactg atagtccttt ttccaatgtt ttattgggga attaaatagt gtgatgtttg    2820
gattgatatc gtgaaatcct cagccgagaa attgggctgg attgtgcttt ggttaataca    2880
tctttcccta aagaagataa acacaaaatc cattccaggt agctcggcac caactaagaa    2940
aaaaagcaca aagttctcag agctctcgag gaaagtggtt gtccccgtac caccatgcac    3000
tgtaaatatc cctcccctct ctccctggtc ccctccccca tccccaccac tgatatcatg    3060
gggagtaata ggaccagagc ggtatctctg gcaccacact agggactatc aggtaataaa    3120
agctttgact ccctgaaaaa aaaaaaaaaa aaa                                 3153

<210> SEQ ID NO 4
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 4
gacattaagg aatgccttac ccaca                                            25

<210> SEQ ID NO 5
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 5
gtgtctcatc tgaaatcaag acaac                                            25
```

MODULATION OF PTPRA TO TREAT ARTHRITIS

CROSS-REFERENCES TO RELATED APPLICATIONS

This application is the national state filing under U.S.C. 371 of international application PCT/US2015/049228, filed Sep. 9, 2015, which claims the benefit of U.S. Provisional Pat. Application No. 62/048,129, filed Sep. 9, 2014, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under AR47825, AI070555 and UL1TR000100 awarded by the National Institute of Health. The government has certain rights in the invention.

BACKGROUND

Fibroblast-like synoviocytes (FLS) in the intimal lining of the joint synovium control the composition of the synovial fluid and extracellular matrix (ECM) of the joint lining. In rheumatoid arthritis (RA), FLS become aggressive and invasive, contributing to many aspects of RA pathology. FLS produce matrix metalloproteinases (MMPs) that break down the ECM, directly invade and digest the articular cartilage, promote bone erosion, and promote inflammation through secretion of interleukin 6 (IL-6), chemokines, and other inflammatory mediators (1-6). FLS are highly sensitive to the inflammatory environment present in rheumatoid joints. Growth factors, especially platelet-derived growth factor (PDGF), stimulate FLS invasiveness. Inflammatory cytokines, particularly tumor necrosis factor-alpha (TNF) and interleukin-1 (IL-1), enhance FLS aggressiveness, proinflammatory features and MMP production (5, 6). Targeting of molecules that control FLS invasiveness and inflammatory output is being considered an option for development of new therapies for RA (7-9).

Many signaling pathways controlling FLS behavior rely upon phosphorylation of proteins on tyrosine residues (8), which results from the balanced action of protein tyrosine kinases (PTKs) and phosphatases (PTPs). Applicants recently profiled the expression of PTPs in FLS from RA patients (RA FLS), and showed that PTPN11, encoding the SH2-domain containing PTP 2 (SHP-2), is overexpressed in RA FLS compared to FLS from osteoarthritis (OA) patients (10). Functional studies revealed that SHP-2 mediates the aggressive phenotype of RA FLS by promoting activation of focal adhesion kinase (FAK), leading to enhanced survival, invasiveness, and responsiveness to PDGF and TNF stimulation (10). FAK is a ubiquitously expressed non-receptor tyrosine kinase that acts as a critical mediator of cell motility and invasiveness (11) and promotes cell resistance to apoptosis (12). FAK activation is dependent upon phosphorylation on Tyr397 induced by integrin-mediated cell adhesion (11,12). This site can be autophosphorylated by FAK or phosphorylated by SRC family kinases (SFKs). Phospho-Tyr397 provides a docking site for SFKs, which phosphorylate other tyrosine residues of FAK, resulting in FAK activation. FAK may act as an important mediator of the anomalous behavior of RA FLS. Increased levels of phospho-FAK were shown in lining cells from RA synovial tissue compared to normal tissue (13). Importantly a recent epigenomics study showed that the FAK pathway is a hotspot of epigenetic anomalies in RA FLS (14).

RPTPα, encoded by the PTPRA gene, is a ubiquitously expressed PTP (17, 18). RPTPα is a critical positive regulator of signaling through dephosphorylation of the SFK C-terminal inhibitory tyrosine residue (Tyr527 in SRC) (16, 18-20). Dephosphorylation of SRC-Tyr527 enhances SRC activation, leading to tyrosine phosphorylation of FAK and other substrates. Fibroblasts from PTPRA KO mice showed increased phosphorylation of SRC-Tyr527, reduced SFK tyrosine kinase activity, reduced phosphorylation of FAK-Tyr397, and reduced SRC/FAK association (15, 20).

There are provided herein, inter alia, methods and compositions for treatment of autoimmune diseases including invasiveness of FLS in RA.

BRIEF SUMMARY OF THE INVENTION

In a first aspect, there is provided a method of treating an autoimmune disease in a subject in need thereof, the method including administering to the subject an effective amount of a PTPRA antagonist.

In another aspect, there is provided a method of decreasing inflammation in a synovium of a subject in need thereof, the method including administering to the subject an effective amount of a PTPRA antagonist.

In another aspect, there is provided a method of decreasing expression of PTPRA in a fibroblast-like synoviocyte, the method including contacting said fibroblast-like synoviocyte with an effective amount of a PTPRA antagonist.

In another aspect, there is provided a method of decreasing TNF activity, IL-1 activity or PDGF activity in a fibroblast-like synoviocyte, the method including contacting the fibroblast-like synoviocyte with an effective amount of a PTPRA antagonist.

In another aspect, there is provided a method of decreasing invasiveness or migration of a fibroblast-like synoviocyte, the method including contacting the fibroblast-like synoviocyte with an effective amount of a PTPRA antagonist.

In another aspect, there is provided a pharmaceutical composition including a PTPRA antagonist and a pharmaceutically acceptable excipient.

In another aspect, a method of treating an autoimmune disease in a subject in need thereof is provided. The method includes administering to the subject an effective amount of a protein tyrosine phosphatase receptor type A (PTPRA) antagonist, thereby treating an autoimmune disease in said subject.

In another aspect, a method of identifying a PTPRA antagonist is provided. The method includes contacting a test agent with a sarcoma tyrosine kinase (SRC)-expressing cell in vitro, thereby forming a contacted cell. In the contacted cell a level of SRC Tyr527 phosphorylation is determined, wherein an increased level of SRC Tyr527 phosphorylation indicates the test agent is a PTPRA antagonist, thereby identifying a PTPRA antagonist.

In another aspect, a method of identifying a PTPRA antagonist is provided. The method includes contacting a test agent with a focal adhesion kinase (FAK)-expressing cell in vitro, thereby forming a contacted cell. In the contacted cell a level of FAK Tyr397 phosphorylation is determined, wherein a decreased level of FAK Tyr397 phosphorylation indicates the test agent is a PTPRA antagonist, thereby identifying a PTPRA antagonist.

In another aspect, a method of decreasing inflammation in a synovium of a subject in need thereof is provided. The method includes administering to the subject an effective amount of a PTPRA antagonist, wherein the PTPRA antagonist is an anti-PTPRA antibody, an anti-PTPRA inhibitory nucleic acid, peptide, or a small molecule.

In another aspect, a method of inhibiting PTPRA protein activity in a cell is provided. The method includes contacting a cell with an effective amount of a PTPRA antagonist thereby inhibiting PTPRA protein activity in the cell.

BRIEF DESCRIPTION OF THE DRAWINGS

FIG. 1A: Immunohistochemical staining of RA synovial sections using anti-RPTPα or control IgG antibodies. FIG. 1B: PTPRA mRNA expression levels were measured by qPCR. Median and interquartile range (IQR) is shown. *, $p<0.05$, Mann-Whitney test. RA FLS (n=4) were treated with 2.5 µM control non-targeting (Ctl) or PTPRA PMO for 7 d. FIG. 1C: RPTPα protein levels were measured by Western blotting. RA FLS (n=4) were treated with 2.5 µM control non-targeting (Ctl) or PTPRA PMO for 7 d. FIG. 1D: Following treatment with PMO, RA FLS (n=4) were stimulated with 50 ng/ml TNF or 2 ng/ml IL-1β for 24 hr. mRNA expression was analyzed by qPCR. Median and IQR is shown. Protein expression in cell supernatants was measured by ELISA. Mean±standard error of the mean (SEM) is shown. *, $p<0.05$, Mann-Whitney test.

FIG. 2A: Following treatment with PMO for 7 d, RA FLS (n=4) invaded through Matrigel-coated transwell chambers in response to 50 ng/ml PDGF-BB for 48 hr. Median and IQR % maximum number of cells per field is shown. *, $p<0.05$, Mann-Whitney test. FIG. 2B: PMO-treated RA FLS (n=4) migrated through uncoated transwell chambers in response to 5% FBS for 24 hr. Median and IQR % maximum number of cells per field is shown. *, $p<0.05$, Mann-Whitney test. FIG. 2C: PMO-treated RA FLS were washed and stimulated with 50 ng/ml PDGF for 24 hr. Cells were collected and stained with Annexin V and PI, and cell fluorescence was assessed by FACS. Graphs show gating strategy to detect early apoptotic (Annexin V$^+$PI$^-$) and necrotic/late apoptotic (Annexin V$^+$PI$^+$) cells. Significance was calculated using the Chi square test (p<0.0001, Chi-square=2294, df=2). Data is representative of 4 independent experiments. FIG. 2D: PMO-treated RA FLS (n=4) were plated on fibronectin (FN)-coated coverslips in the presence of 5% FBS. Graphs show median and IQR cells per field after 15 min (left) or cell area after 15, 30 and 60 min (right). *, $p<0.05$, Wilcoxon matched-pairs signed rank test.

FIG. 3A: anti-pSRC-Y527 levels in PMO-treated RA FLS lysates were measured by Western blotting. Data is representative of 4 independent experiments. Western blotting of lysates of PMO-treated RA FLS stimulated with 50 ng/ml TNF or left unstimulated. FIG. 3B: Signal intensities of Western blots of TNF-activated proteins from lysates were quantified by densitometric scanning. Mean±SEM of signal relative to GAPDH from 6 RA FLS lines is shown. FIG. 3C: Representative image is shown. FIG. 3D: Signal intensities of Western blots of lysates of unstimulated PMO-treated RA FLS. Mean±SEM of signal relative to p65 from 6 RA FLS lines is shown. *, p<0.05; NS, non-significant, Wilcoxon matched-pairs signed rank test.

FIG. 4A: RA FLS (n=4) were stimulated with 50 ng/ml TNFα or 2 ng/ml IL-1β in the presence of DMSO, the FAK inhibitor PF573228, or the AKT inhibitor MK2206 for 24 hr. mRNA expression was analyzed by qPCR. Mean±SEM is shown. *, p<0.05, Mann-Whitney test. FIG. 4B: RA FLS were stimulated with 50 ng/ml TNF or 2 ng/ml IL-1β for 30 min or left unstimulated, in the presence of DMSO or 10 µM FAK inhibitor PF573228. Data is representative of 4 independent experiments.

FIG. 5A: Ankle thickness was measured every 2 days (WT, n=16; KO, n=17). Mean±SEM ankle swelling is shown. *, p<0.05, 2-way ANOVA. FIG. 5B: 7 days post-sera transfer, mice (n=3) were injected with intravital inflammation probe and luminescence of wrist and ankle joints was measured. Mean±SEM luminescent counts per joint are shown. *, p<0.05, Wilcoxon matched-pairs signed rank test. FIG. 5C: Histological analysis of ankles stained with H&E or Safranin-O at the end of the disease course. The left panel shows histological scores of bone and cartilage erosions (WT, n=16; KO, n=17). Mean±SEM is shown. *, p<0.05, Wilcoxon matched-pairs signed rank test. The right panel shows representative images of H&E-stained (upper panels; arrows indicate regions of inflammatory infiltrate) or Safranin-O-stained (lower panels; arrows indicate regions of cartilage erosion) joints.

FIG. 6A: Mice were lethally irradiated and administered bone-marrow from donor mice. After 10-11 weeks post-irradiation, arthritis was induced in recipients by administration of K/BxN sera. Male WT congenic CD45.1 mice were administered bone-marrow cells from WT or Ptpra KO CD45.2 donor mice (WT donors, n=19; KO donors, n=18). FIG. 6B: Mice were lethally irradiated and administered bone-marrow from donor mice. After 10-11 weeks post-irradiation, arthritis was induced in recipients by administration of K/BxN sera. Male WT (n=11) or Ptpra KO (n=11) mice were administered bone-marrow cells from WT congenic CD45.1 mice. Mean±SEM is shown. *, p<0.05, 2-way ANOVA. FIG. 6C: WT (n=5) and Ptpra KO (n=3) littermate mice were administered Angiosense 680 dye, followed by administration of K/BxN serum. Ankle fluorescence was monitored after 60 min. Median and IQR is shown. NS, non-significant, Mann-Whitney test. FIG. 6D: WT (n=7) or Ptpra KO (n=7) mice were administered K/BxN sera. Following 8 days post-sera transfer, ankle joints were homogenized and mRNA expression was analyzed by qPCR. Median and IQR is shown. *, p<0.05, NS, non-significant, Mann-Whitney test.

FIG. 7A: Representative images of H&E-stained joints from FIG. 5C. Arrows indicate inflammatory infiltrate. FIG. 7B: MicroCT analysis of ankles at the end of the disease course. Quantification of periosteal bone mineralization (WT, n=8; KO, n=10). Mean±SEM is shown. *, p<0.05, Wilcoxon matched pairs signed rank test. FIG. 7C: Representative images of bones from FIG. 7B. Arrows indicate areas of distinct cortical bone thickening with periosteal mineralization.

FIG. 8A: Following treatment of RA FLS (n=4)

with 2.5 μM Ctl or PTPRA_2 PMO for 7 d, PTPRA mRNA expression levels were measured by qPCR. Median±IQR is shown. *, p<0.05, Mann-Whitney test. FIG. 8B: Following treatment with PMO, RA FLS (n=4) were stimulated with 50 ng/ml TNF or 2 ng/ml IL-1 for 24 hr. Protein expression was measured in cell supernatants by ELISA. Median±IQR is shown. *, p<0.05, Mann-Whitney test.

FIG. 10A: At 8 days post-serum transfer, mice were injected with the Xenolight RediJect Inflammation probe and luminescence was measured. Representative image of mice from FIG. 5B. FIG. 10B: Histological analysis of ankles stained with Safranin O at the end of the K/BxN arthritis disease course. Representative images of Safranin-O-stained joints from FIG. 5C. FIG. 10C: Representative image of ankle joints from FIGS. 7B-7C. Cross-sections of the calcaneus and tibia/fibula further show cortical bone periosteal mineralization.

FIGS. 11A-1B. RPTPα is expressed in the RA synovial lining. FIG. 11A: Immunohistochemical staining of arthritic joints from WT and Ptpra KO mice (from FIG. 5A) using anti-RPTPα antibody.

DETAILED DESCRIPTION

I. Definitions

Figure 1A:
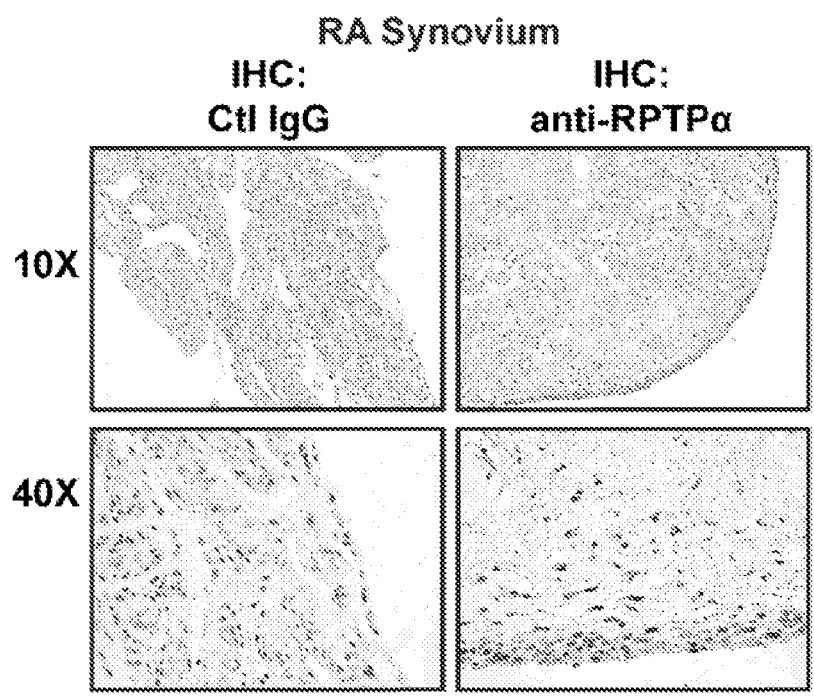
FIGS. 1A-1D. RPTPα is enriched in the RA synovial lining and promotes TNF and IL-1β signaling in RA FLS.

The terms "PTPR," "RPTP," "rPTP" and the like refer, in the usual and customary sense, to receptor-type protein tyrosine phosphatases, which are found in nature as membrane bound protein tyrosine phosphatases. In embodiments, the RPTP is a mammalian RPTP (e.g. human, mouse, rat, or other mammal). In embodiments, the RPTP is a human RPTP. In embodiments, the RPTP refers to the protein encoded by the gene PTPRA. It is understood that the term "PTPRA" in the context of a gene refers to the gene encoding receptor tyrosine-protein phosphatase alpha. It is further understood that the terms "PTPRA," "RPTPα," "RPTPa" and the like in the context of a protein refer to receptor tyrosine-protein phosphatase alpha. In embodiments, RPTP means the full length RPTP (e.g. the protein translated from the complete coding region of the gene, which may also include post-translational modifications). In embodiments RPTP includes a fragment of the RPTP full length protein or a functional fragment of the full length RPTP protein. In embodiments this definition includes one or all splice variants of an RPTP. An RPTP may include all homologs of the RPTP. In embodiments, PTPRA refers to mammalian PTPRA. In embodiments, a PTPRA refers to a human PTPRA. In embodiments, an RPTP includes all splice variants of the RPTP. In embodiments, an RPTP may refer to 1, 2, 3, 4, 5, 6, 7, 8, 9, 10, or more splice variants.

The term "PTPRA" as provided herein includes any of the receptor-type tyrosine-protein phosphatase alpha (PTPRA) naturally occurring forms, homologs or variants that maintain the phosphatase activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the PTPRA protein is the protein as identified by the NCBI sequence reference GI:4506303. In embodiments, the PTPRA protein is encoded by a nucleic acid sequence identified by the NCBI sequence reference GI:125987583. In embodiments, the PTPRA protein is encoded by a nucleic acid sequence of SEQ ID NO:1, SEQ ID NO:2 or SEQ ID NO:3.

The term "SRC" as provided herein includes any of sarcoma tyrosine kinase (SRC) naturally occurring forms, homologs or variants that maintain the kinase activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the SRC protein is the protein as identified by the NCBI sequence reference GI:4885609. In embodiments, the SRC protein is encoded by a nucleic acid sequence identified by the NCBI sequence reference GI:520262038.

The term "FAK" as provided herein includes any of the focal adhesion kinase (FAK) naturally occurring forms, homologs or variants that maintain the kinase activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the FAK protein is the protein as identified by the NCBI sequence reference GI:313851044. In embodiments, the FAK protein is encoded by a nucleic acid sequence identified by the NCBI sequence reference GI:313851043.

The term "SRC Tyr527" as provided herein refers to a tyrosine residue corresponding to position 527 in a SRC protein. The term "corresponding to," when used in the context of the numbering of a given amino acid or polynucleotide sequence, refers to the numbering of the residues of a specified reference sequence when the given amino acid or polynucleotide sequence is compared to a reference sequence (e.g., the NCBI sequence reference GI:4885609). In embodiments, the reference sequence is a SRC protein having the sequence of GI:4885609.

The term "FAK Tyr397" as provided herein refers to a tyrosine residue corresponding to position 397 in a FAK protein. The term "corresponding to," when used in the context of the numbering of a given amino acid or polynucleotide sequence, refers to the numbering of the residues of a specified reference sequence when the given amino acid or polynucleotide sequence is compared to a reference sequence (e.g., the NCBI sequence reference GI:313851044). In embodiments, the reference sequence is a SRC protein having the sequence of GI:313851044.

A "test agent" as provided herein may be a nucleic acid, peptide, antibody or small molecule. In embodiments, the test agent is a nucleic acid. In embodiments, the test agent is a peptide. In embodiments, the test agent is a small molecule.

The terms "PTPR antagonist," "RPTP antagonist" and the like refer to an agent which reduces the level of activity or a PTPR or the level of expression of a PTPR, e.g., RPTPα.

The term "PTPRA antagonist" refers to an agent which reduces the level of activity or the level of expression of RPTPα. A PTPR antagonist can be a RPTP binding agent, a RPTP small molecule inhibitor, a RPTP allosteric inhibitor, an anti-PTPR antibody, an anti-PTPR inhibitory nucleic acid, an anti-PTPR RNAi molecule, or a PTPR ligand mimetic, as disclosed herein.

The terms "subject," "patient," "individual," etc. are not intended to be limiting and can be generally interchanged. That is, an individual described as a "patient" does not necessarily have a given disease, but may be merely seeking medical advice.

A "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (i.e., non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, individual RPTP levels, specific cell types, specific bodily fluids, specific tissues, synoviocytes, synovial fluid, synovial tissue, fibroblast-like synoviocytes, macrophage-like synoviocytes, and the like).

One of skill in the art will understand which standard controls are most appropriate in a given situation and be able to analyze data based on comparisons to standard control values. Standard controls are also valuable for determining the significance (e.g. statistical significance) of data, as known in the art.

The terms "dose" and "dosage" are used interchangeably herein. A dose refers to the amount of active ingredient given to an individual at each administration, or to an amount administered in vitro or ex vivo. For the methods and compositions provided herein, the dose may generally depend to the required treatment for the disease (e.g. an autoimmune, inflammatory autoimmune, cancer, infectious, immune, or other disease), and the biological activity of the RPTP binding agent, RPTP antagonist, anti-PTPR antibody, anti-PTPR inhibitory nucleic acid, anti-PTPR RNAi molecule, or PTPR ligand mimetic. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" may refer to any delay in onset, reduction in the frequency or severity of symptoms, amelioration of symptoms, reduction in risk of developing symptoms, improvement in patient comfort or function (e.g. joint function), decrease in severity of the disease state, etc. The effect of treatment can be compared to an individual or pool of individuals not receiving a given treatment, or to the same patient prior to, or after cessation of, treatment. The term "prevent" generally refers to a decrease in the occurrence of a given disease (e.g. an autoimmune, inflammatory autoimmune, cancer, infectious, immune, or other disease) or disease symptoms in a patient. As indicated above, the prevention may be complete (no detectable symptoms) or partial, such that fewer symptoms are observed than would likely occur absent treatment.

By "effective amount," "therapeutically effective amount," "therapeutically effective dose or amount" and the like as used herein is meant an amount (e.g., a dose) that produces effects for which it is administered (e.g. treating or preventing a disease). The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The term "diagnosis" refers to a relative probability that a disease (e.g. an autoimmune, inflammatory autoimmune, cancer, infectious, immune, or other disease) is present in the subject. The term "prognosis" refers to a relative probability that a certain future outcome may occur in the subject with respect to a disease state. For example, in the present context, prognosis can refer to the likelihood that an individual will develop a disease (e.g. an autoimmune, inflammatory autoimmune, cancer, infectious, immune, or other disease), or the likely severity of the disease (e.g., extent of pathological effect and duration of disease). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, or even longer. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe bound to the probe may be detected by detecting the presence of the label bound to the probe. Alternatively, a method using high affinity interactions may achieve the same results where one of a pair of binding partners binds to the other, e.g., biotin, streptavidin.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent hybridization conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

Nucleic acids may be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

An "inhibitory nucleic acid" is a nucleic acid (e.g. DNA, RNA, polymer of nucleotide analogs) that is capable of binding to a target nucleic acid (e.g. an mRNA translatable into an RPTP) and reducing transcription of the target nucleic acid (e.g. mRNA from DNA) or reducing the translation of the target nucleic acid (e.g., mRNA) or altering transcript splicing (e.g. single stranded morpholino oligo). A "morpholino oligo" may be alternatively referred to as a "morphlino nucleic acid" and refers to morpholine-containing nucleic acid nucleic acids commonly known in the art (e.g. phosphoramidate morpholinio oligo or a "PMO"). See Marcos, P., *Biochemical and Biophysical Research Communications* 358 (2007) 521-527. In embodiments, the "inhibitory nucleic acid" is a nucleic acid that is capable of binding (e.g. hybridizing) to a target nucleic acid (e.g. an mRNA translatable into an RPTP) and reducing translation of the target nucleic acid. The target nucleic acid is or includes one or more target nucleic acid sequences to which the inhibitory nucleic acid binds (e.g. hybridizes). Thus, an inhibitory nucleic acid typically is or includes a sequence (also referred to herein as an "antisense nucleic acid sequence") that is capable of hybridizing to at least a portion of a target nucleic acid at a target nucleic acid sequence. An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In embodiments, the inhibitory nucleic acid is single stranded. In embodiments, the inhibitory nucleic acid is double stranded.

An "antisense nucleic acid" is a nucleic acid (e.g. DNA, RNA or analogs thereof) that is at least partially complementary to at least a portion of a specific target nucleic acid (e.g. a target nucleic acid sequence), such as an mRNA molecule (e.g. a target mRNA molecule) (see, e.g., Weintraub, *Scientific American*, 262:40 (1990)), for example antisense, siRNA, shRNA, shmiRNA, miRNA (micro-RNA). Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone-modified nucleotides. An "anti-PTPR antisense nucleic acid" is an antisense nucleic acid that is at least partially complementary to at least a portion of a target nucleic acid sequence, such as an mRNA molecule, that codes at least a portion of the PTPR. An "PTPRA antisense nucleic acid" is an antisense nucleic acid that is at least partially complementary to at least a portion of a target nucleic acid sequence, such as an mRNA molecule, that codes at least a portion of RPTPα.

In embodiments, an antisense nucleic acid is a morpholino oligo. In embodiments, a morpholino oligo is a single stranded antisense nucleic acid, as is know in the art. In embodiments, a morpholino oligo decreases protein expression of a target, reduces translation of the target mRNA, reduces translation initiation of the target mRNA, or modifies transcript splicing. In embodiments, the morpholino oligo is conjugated to a cell permeable moiety (e.g. peptide). Antisense nucleic acids may be single or double stranded nucleic acids.

In the cell, the antisense nucleic acids may hybridize to the target mRNA, forming a double-stranded molecule. The antisense nucleic acids, interfere with the translation of the mRNA, since the cell will not translate a mRNA that is double-stranded. The use of antisense methods to inhibit the in vitro translation of genes is well known in the art (Marcus-Sakura, *Anal. Biochem.*, 172:289, (1988)). Antisense molecules which bind directly to the DNA may be used.

Inhibitory nucleic acids can be delivered to the subject using any appropriate means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. An example of a colloidal system is a liposome.

Liposomes are artificial membrane vesicles which are useful as delivery vehicles in vitro and in vivo. Nucleic acids, including RNA and DNA within liposomes and be delivered to cells in a biologically active form (Fraley, et al., *Trends Biochem. Sci.,* 6:77, 1981). Liposomes can be targeted to specific cell types or tissues using any means known in the art. Inhibitory nucleic acids (e.g. antisense nucleic acids, morpholino oligos) may be delivered to a cell using cell permeable delivery systems (e.g. cell permeable peptides). In embodiments, inhibitory nucleic acids are delivered to specific cells or tissues using viral vectors or viruses.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, *Nature,* 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, *Molecular Interventions,* 2:158 (2002).

The siRNA can be administered directly or siRNA expression vectors can be used to induce RNAi that have different design criteria. A vector can have inserted two inverted repeats separated by a short spacer sequence and ending with a string of T's which serve to terminate transcription.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself Any biopsy technique known in the art can be applied to the diagnostic and prognostic methods disclosed herein. The biopsy technique applied will depend on the tissue type to be evaluated (i.e., prostate, lymph node, liver, bone marrow, blood cell, joint tissue, synovial tissue, synoviocytes, fibroblast-like synoviocytes, macrophage-like synoviocytes, immune cells, hematopoietic cells, fibroblasts, macrophages, T cells, etc.), the size and type of a tumor (i.e., solid or suspended (i.e., blood or ascites)), among other factors. Representative biopsy techniques include excisional biopsy, incisional biopsy, needle biopsy, surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles disclosed herein.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, BIOCONJUGATE TECHNIQUES 1996, Academic Press, Inc., San Diego.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In embodiments, antibodies or fragments of antibodies may be derived from different organisms, including humans, mice, rats, hamsters, camels, etc. Antibodies disclosed herein may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies as disclosed herein and for use according to the methods disclosed herein, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides as disclosed herein. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93

(1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321:522; and Verhoyen et al. (1988) *Science* 239:1534). Humanized antibodies are further described in, e.g., Winter and Milstein (1991) *Nature* 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., *PNAS USA*, 81:6851-6855 (1984), Jones et al., *Nature* 321:522-525 (1986); Riechmann et al., *Nature* 332:323-327 (1988); Morrison and Oi, *Adv. Immunol.*, 44:65-92 (1988), Verhoeyen et al., *Science* 239:1534-1536 (1988) and Presta, *Curr. Op. Struct. Biol.* 2:593-596 (1992), Padlan, *Molec. Immun.*, 28:489-498 (1991); Padlan, *Molec. Immun.*, 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the present disclosure include humanized and/or chimeric monoclonal antibodies.

In embodiments, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme.

The immunoconjugate can be used for targeting the effector moiety to an RPTPa positive cell, i.e., cells which express RPTPa, assay of which can be readily apparent when viewing the bands of gels with approximately similarly loaded with test and controls samples. Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

Additionally, the recombinant proteins disclosed herein including the antigen-binding region of any of the antibodies disclosed herein can be used to treat inflammation. In such a situation, the antigen-binding region of the recombinant protein is joined to at least a drug having therapeutic activity. The second drug can include, but is not limited to, a nonsteroidal anti-inflammatory drug. Suitable nonsteroidal anti-inflammatory drugs include aspirin, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), tolmetin (Tolectin).

Techniques for conjugating therapeutic agents to antibodies are well known (see, e.g., Arnon et al., "Monoclonal Antibodies For Immunotargeting Of Drugs In Cancer Therapy", in MONOCLONAL ANTIBODIES AND CANCER THERAPY, Reisfeld et al. (eds.), pp. 243-56 (Alan R. Liss, Inc. 1985); Hellstrom et al., ANTIBODIES FOR DRUG DELIVERY IN CONTROLLED DRUG DELIVERY (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A*

*Laboratory Manual* (1998) for a description of immunoassay formats and conditions that can be used to determine specific immunoreactivity).

As used herein, the term "pharmaceutically acceptable" is used synonymously with "physiologically acceptable" and "pharmacologically acceptable". A pharmaceutical composition will generally include agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and/or absorption by a subject and can be included in the compositions disclosed herein without causing a significant adverse toxicological effect on the patient. Unless indicated to the contrary, the terms "active agent," "active ingredient," "therapeutically active agent," "therapeutic agent" and like are used synonymously. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. One of skill in the art will recognize that other pharmaceutical excipients are useful in the methods and compositions disclosed herein.

Certain compounds disclosed herein can exist in unsolvated forms as well as solvated forms, including hydrated forms. In general, the solvated forms are equivalent to unsolvated forms and are intended to be encompassed within the scope of the present disclosure. Certain compounds disclosed herein may exist in multiple crystalline or amorphous forms. In general, all physical forms are equivalent for the uses contemplated herein and are intended to be within the scope of the present disclosure.

A "protein level of an RPTP" refers to an amount (relative or absolute) of RPTP in its protein form (as distinguished from its precursor RNA form). A protein of an RPTP may include a full-length protein (e.g. the protein translated from the complete coding region of the gene, which may also include post-translational modifications), functional fragments of the full length protein (e.g. sub-domains of the full length protein that possess an activity or function in an assay), or protein fragments of the RPTP, which may be any peptide or oligopeptide of the full length protein.

An "RNA level of an RPTP" refers to an amount (relative or absolute) of RNA present that may be translated to form an RPTP. The RNA of an RPTP may be a full-length RNA sufficient to form a full-length RPTP. The RNA of an RPTP may also be a fragment of the full length RNA thereby forming a fragment of the full length RPTP. The fragment of the full length RNA may form a functional fragment of the RPTP. In embodiments, the RNA of an RPTP includes all splice variants of an RPTPR gene.

An "autoimmune therapeutic agent" is a molecule (e.g. antibody, nucleic acid, inhibitory nucleic acid, ligand mimetic, small chemical molecule) that treats or prevents an autoimmune disease when administered to a subject in a therapeutically effective dose or amount. In embodiments, an autoimmune therapeutic agent is an RPTP binding agent. In embodiments, the therapeutic agent can bind to more than one RPTP.

An "IAD therapeutic agent" is a molecule that treats or prevents an inflammatory autoimmune disease (IAD) when administered to a subject in a therapeutically effective dose or amount where the autoimmune disease is mediated by a PTPR. Some non-limiting examples of an IAD therapeutic agent include an IAD PTPR binding agent, anti-IAD PTPR antibody, anti-IAD PTPR inhibitory nucleic acid, anti-PTPRA RNAi molecule, and an IAD PTPR ligand mimetic. In embodiments, IAD therapeutic agents are useful in methods and compositions described herein relating to any autoimmune disease. In embodiments, the IAD therapeutic agent can bind to more than one RPTP. In embodiments, the IAD therapeutic agent can bind to RPTPα.

An "RPTP binding agent" is a molecule that binds (e.g. preferentially binds) to one or more RPTPs, RNA that is translatable to an RPTP, or DNA that is transcribable to an RNA that is translatable to an RPTP. Where the molecule preferentially binds, the binding is preferential as compared to other macromolecular biomolecules present in an organism or cell. A compound preferentially binds to as compared to other macromolecular biomolecules present in an organism or cell, for example, when the preferential binding is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, 1,000,000-fold greater. In embodiments, the RPTP binding agent preferentially binds to one or more RPTPs. In embodiments, the RPTP binding agent preferentially binds to one RPTP (e.g. RPTPα) in comparison to one or more other RPTPs. In embodiments, the RPTP binding agent preferentially binds to an RNA that is translatable to an RPTP (e.g. RPTPα) compared to an RNA that is translatable to another RPTP nucleic acids. In embodiments, the RNA is mRNA. In embodiments, the RPTP binding agent is a protein, nucleic acid, ligand, ligand mimetic, or a small chemical molecule. In embodiments, an RPTP binding agent disrupts the interaction between an RPTP and a physiological or natural ligand. In embodiments, an RPTP binding agent binds a physiological or natural ligand of the RPTP. In embodiments, an RPTP binding agent binds the complex of an RPTP bound to a ligand. In embodiments, the binding agent can bind to more than one RPTP. An "RPTPα binding agent" or "PTPRA binding agent" is an RPTP binding agent that binds RPTPα.

An "anti-PTPR antibody" is an antibody, as disclosed herein and well known in the art, directed to a PTPR. The term "anti-PTPRA antibody" and the like refer to an antibody directed to RPTPα.

An "anti-PTPR inhibitory nucleic acid" is an inhibitory nucleic acid that is capable of hybridizing to target nucleic acid sequence (e.g. an mRNA sequence) that is translatable to a PTPR (e.g., RPTPα) or a target nucleic acid sequence (e.g. a DNA sequence) that is transcribable to an RNA that is translatable to a PTPR. The anti-PTPR inhibitory nucleic acid is typically capable of decreasing the amount of PTPR that is translated in a cell. An "anti-PTPRA inhibitory nucleic acid" is an inhibitory nucleic acid that is capable of hybridizing to target nucleic acid sequence (e.g. an mRNA sequence) that is translatable to RPTPα or a target nucleic acid sequence (e.g. a DNA sequence) that is transcribable to an RNA that is translatable to RPTPα.

An "anti-PTPR RNAi molecule" is an siRNA, shRNA, miRNA, shmiRNA, or other nucleic acid, as well known in the art, that is capable of inducing RNAi and hybridizing to an RNA that is translatable to a PTPR. The anti-PTPR RNAi molecule is typically capable of decreasing the amount of PTPR that is translated in a cell. An anti-PTPRA RNAi molecule" is an siRNA, shRNA, miRNA, shmiRNA, or other nucleic acid, as well known in the art, that is capable of inducing RNAi and hybridizing to an RNA that is translatable to a RPTPα.

A "PTPR ligand mimetic" is a PTPR binding agent that is designed to mimic, in structure or in binding mode, a known PTPR ligand or is capable of inhibiting the binding of a natural or physiological ligand to a PTPR. In embodiments, a PTPR ligand mimetic is a synthetic chemical compound, peptide, protein, fusion protein (e.g., PTPR-Fc), peptidomimetic, or modified natural ligand. For example, a PTPR ligand mimetic may bind the same amino acids or a subset of the same amino acids on the PTPR that a natural ligand of the PTPR binds during the physiological functioning of the PTPR. PTPR ligand mimetics include biopolymers (e.g. proteins, nucleic acids, or sugars), lipids, chemical molecules with molecular weights less than five hundred (500) Daltons, one thousand (1000) Daltons, five thousand (5000) Daltons, less than ten thousand (10,000) Daltons, less than twenty five thousand (25,000) Daltons, less than fifty thousand (50,000) Daltons, less than seventy five thousand (75,000), less than one hundred thousand (100,000), or less than two hundred fifty thousand (250,000) Daltons. In embodiments, the synthetic chemical compound is greater than two hundred fifty thousand (250,000) Daltons. In certain embodiments, the PTPR binding agent is less than five hundred (500) Daltons. In embodiments, a PTPR ligand mimetic is a protein. A "PTPRA ligand mimetic" is a PTPRA binding agent that is designed to mimic, in structure or in binding mode, a known RPTPα ligand or is capable of inhibiting the binding of a physiological ligand to RPTPα.

In embodiments, a PTPR ligand mimetic is a small chemical molecule. The term "small chemical molecule" and the like, as used herein, refers to a molecule that has a molecular weight of less than two thousand (2000) Daltons. In embodiments, a small chemical molecule is a molecule that has a molecular weight of less than one thousand (1000) Daltons. In other embodiments, a small chemical molecule is a molecule that has a molecular weight of less than five hundred (500) Daltons. In other embodiments, a small chemical molecule is a molecule that has a molecular weight of less than five hundred (500) Daltons. In other embodiments, a small chemical molecule is a molecule that has a molecular weight of less than one hundred (100) Daltons.

In embodiments, a RPTP inhibitor is a small molecule. In embodiments the inhibitor is an inhibitor of RPTP enzymatic activity. In other embodiments the inhibitor is a allosteric inhibitor of RPTP.

An agent may "target" an RPTP, a nucleic acid (e.g. RNA or DNA) of an RPTP, or a protein of an RPTP, by binding (e.g. preferentially binding) to the RPTP, nucleic acid (e.g. RNA or DNA) of an RPTP, or protein of an RPTP. Where preferentially binding, the agent binds preferentially to a targeted molecule compared to its binding to other molecules of a similar form (e.g. other RPTPs if the agent targets an RPTP). An agent preferentially binds to a molecule, for example, when the binding to the targeted molecule is greater than the binding to other molecules of a similar form. In embodiments, the preferential binding is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, 1,000,000-fold greater. In embodiments, an agent targets an RPTP (e.g. RPTPα), a nucleic acid (e.g. RNA or DNA) of an RPTP (e.g. RPTPα), or a protein of an RPTP (e.g. RPTPα), when a binding assay or experiment (e.g. gel electrophoresis, chromatography, immunoassay, radioactive or non-radioactive labeling, immunoprecipitation, activity assay, etc.) reveals only an interaction or primarily an interaction with a single RPTP, a nucleic acid (e.g. RNA or DNA) of a single RPTP, or a protein of a single RPTP. An agent may also "target" an RPTP, a nucleic acid (e.g. RNA or DNA) of an RPTP, or a protein of an RPTP by binding to the RPTP, nucleic acid (e.g. RNA or DNA) of an RPTP, or protein of an RPTP, by decreasing or increasing the amount of RPTP in a cell or organism relative to the absence of the agent, or decreasing the interaction between the RPTP with a physiological or natural ligand. A person having ordinary skill in the art, using the guidance provided herein, may easily determine whether an agent decreases or increases the amount of an RPTP in a cell or organism.

II. Methods

In a first aspect, there is provided a method of treating an autoimmune disease in a subject in need thereof, the method including administering to the subject an effective amount of a PTPRA antagonist.

In embodiments, the autoimmune disease is a fibroblast mediated disease, arthritis, osteoarthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome,vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, scleroderma, systemic sclerosis, or allergic asthma.

In embodiments, the autoimmune disease is arthritis. In embodiments, the autoimmune disease is rheumatoid arthritis. In embodiments, the autoimmune disease is psoriatic arthritis. In embodiments, the disease is non-autoimmune arthritis. In embodiments, the non-autoimmune arthritis is osteoarthritis.

In embodiments, the disease is a fibroblast mediated disease. In embodiments, the fibroblast mediated disease includes idiopathic pulmonary fibrosis, fibrotic lung diseases, scleroderma, liver fibrosis, liver sclerosis, advanced glomerulonephritis, nephrosclerosis.

In another aspect, there is provided a method of decreasing inflammation in a synovium of a subject in need thereof, the method including administering to the subject an effective amount of a PTPRA antagonist.

Further to any aspect or embodiment of a method of treating an autoimmune disease or method of decreasing inflammation in a synovium, in embodiments the subject presents with fibroblast-like synoviocytes that express high levels of PTPRA relative to a standard control as disclosed herein. In embodiments, the subject has rheumatoid arthritis.

In another aspect, there is provided a method of decreasing expression of PTPRA in a fibroblast-like synoviocyte, the method including contacting the fibroblast-like synoviocyte (FLS) with an effective amount of a PTPRA antagonist.

In embodiments, the method includes decreasing TNF activity, PDGF activity or IL-1 activity. In embodiments, the method includes decreasing TNF activity. In embodiments, the method includes decreasing PDGF activity. In embodiments, the method including decreasing IL-1 activity.

In embodiments, the method includes decreasing expression of TNF activity PDGF activity or IL-1 activity. In embodiments, the method includes decreasing expression of TNF activity. In embodiments, the method includes decreasing expression of PDGF activity. In embodiments, the method including decreasing expression of IL-1 activity.

In another aspect, there is provided a method of decreasing invasiveness or migration of a fibroblast-like synoviocyte, the method including contacting the fibroblast-like synoviocyte with an effective amount of a PTPRA antagonist.

Further to any aspect or embodiment of a method for decreasing expression of PTPRA in a fibroblast-like synoviocyte, the method includes decreasing TNF activity, IL-1 activity or PDGF activity in a fibroblast-like synoviocyte, or decreasing expression of TNF or ILL In embodiments, the fibroblast-like synoviocyte is a rheumatoid arthritis fibroblast-like synoviocyte. The term "rheumatoid arthritis fibroblast-like synoviocyte" refers to an FLS constituted within or obtained from a subject having rheumatoid arthritis or an FLS that causes, extends or exacerbates RA or symptoms thereof. In embodiments, the fibroblast-like synoviocyte expresses high levels of PTPRA relative to a standard control (e.g. a non-rheumatoid arthritis fibroblast-like synoviocyte).

Further to any aspect or embodiment disclosed above, in embodiments the PTPRA antagonist is an anti-PTPRA antibody, an anti-PTPRA inhibitory nucleic acid or a PTPRA ligand mimetic.

In embodiments, the anti-PTPRA antibody is an anti-PTPRA extracellular antibody. The term "extracellular antibody" in this context refers to an antibody which is directed to an extracellular portion of a target molecule. For example, RPTPα is expressed as a transmembrane precursor protein that undergoes proteolytic cleavage to generate two non-covalently attached subunits, an N-terminal extracellular subunit, and a C-terminal subunit containing the intracellular and transmembrane regions and a small extracellular region. Thus, an anti-PTPRA extracellular antibody is directed to the extracellular portion of RPTPα.

In embodiments, the anti-PTPRA antibody is an anti-PTPRA dimer inhibiting antibody or an anti-PTPRA dimerizing antibody. The term "dimer inhibiting antibody" refers, in the usual and customary sense, to an antibody which binds a target thereby inhibiting dimerization of the target to form a dimer of target molecules. The term "dimerizing antibody" refers, in the usual and customary sense, to an antibody (e.g., a multivalent antibody, e.g., a divalent antibody) which can bind a plurality (e.g., two) target molecules, thereby forming a dimer of target molecules. In embodiments, the anti-PTPRA antibody is an anti-PTPRA dimer inhibiting antibody. In embodiments, the anti-PTPRA antibody is an anti-PTPRA dimerizing antibody.

In embodiments, the anti-PTPRA inhibitory nucleic acid has at least 50% sequence identity (e.g., 50%, 55%, 60%, 65%, 70%, 75%, 80%, 85%, 90%, 95%, 96%, 97%, 98%, 99% or even 100%) to a contiguous sequence of SEQ ID NO:1, SEQ ID NO:2 or SEQ ID NO:3 spanning at least 10 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or even greater).

In embodiments, the anti-PTPRA inhibitory nucleic acid has at least 60% sequence identity (e.g., 60%, 65%, 70%, 75%, 80%, 85%, 90%, 95%, 96%, 97%, 98%, 99% or even 100%) to a contiguous sequence of SEQ ID NO:1, SEQ ID NO:2 or SEQ ID NO:3 spanning at least 10 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or even greater).

In embodiments, the anti-PTPRA inhibitory nucleic acid has at least 70% sequence identity (e.g., 70%, 75%, 80%, 85%, 90%, 95%, 96%, 97%, 98%, 99% or even 100%) to a contiguous sequence of SEQ ID NO:1, SEQ ID NO:2 or SEQ ID NO:3 spanning at least 10 nucleotides (e,g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or even greater).

In embodiments, the anti-PTPRA inhibitory nucleic acid has at least 80% sequence identity (e.g., 80%, 85%, 90%, 95%, 96%, 97%, 98%, 99% or even 100%) to a contiguous sequence of SEQ ID NO:1, SEQ ID NO:2 or SEQ ID NO:3 spanning at least 10 nucleotides (e,g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or even greater).

In embodiments, the anti-PTPRA inhibitory nucleic acid has at least 90% sequence identity (e.g., 90%, 91%, 92%, 93%, 94%, 96%, 97%, 98%, 99% or even 100%) to a contiguous sequence of SEQ ID NO:1, SEQ ID NO:2 or SEQ ID NO:3 spanning at least 10 nucleotides (e,g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or even greater).

In embodiments, the anti-PTPRA inhibitory nucleic acid has at least 50% sequence identity to a contiguous sequence of SEQ ID NO:1, SEQ ID NO:2 or SEQ ID NO:3 spanning at least 10 nucleotides.

In embodiments, the anti-PTPRA inhibitory nucleic acid has at least 60% sequence identity to a contiguous sequence of SEQ ID NO:1, SEQ ID NO:2 or SEQ ID NO:3 spanning at least 10 nucleotides.

In embodiments, the anti-PTPRA inhibitory nucleic acid has at least 70% sequence identity to a contiguous sequence of SEQ ID NO:1, SEQ ID NO:2 or SEQ ID NO:3 spanning at least 10 nucleotides.

In embodiments, the anti-PTPRA inhibitory nucleic acid has at least 80% sequence identity to a contiguous sequence of SEQ ID NO:1, SEQ ID NO:2 or SEQ ID NO:3 spanning at least 10 nucleotides.

In embodiments, the anti-PTPRA inhibitory nucleic acid has at least 90% sequence identity to a contiguous sequence of SEQ ID NO:1, SEQ ID NO:2 or SEQ ID NO:3 spanning at least 10 nucleotides.

In embodiments, the anti-PTPRA inhibitory nucleic acid has at least 50% sequence identity to a contiguous sequence of SEQ ID NO:1, SEQ ID NO:2 or SEQ ID NO:3 spanning at least 15 nucleotides.

In embodiments, the anti-PTPRA inhibitory nucleic acid has at least 60% sequence identity to a contiguous sequence of SEQ ID NO:1, SEQ ID NO:2 or SEQ ID NO:3 spanning at least 15 nucleotides.

In embodiments, the anti-PTPRA inhibitory nucleic acid has at least 70% sequence identity to a contiguous sequence of SEQ ID NO:1, SEQ ID NO:2 or SEQ ID NO:3 spanning at least 15 nucleotides.

In embodiments, the anti-PTPRA inhibitory nucleic acid has at least 80% sequence identity to a contiguous sequence of SEQ ID NO:1, SEQ ID NO:2 or SEQ ID NO:3 spanning at least 15 nucleotides.

In embodiments, the anti-PTPRA inhibitory nucleic acid has at least 90% sequence identity to a contiguous sequence of SEQ ID NO:1, SEQ ID NO:2 or SEQ ID NO:3 spanning at least 15 nucleotides.

In embodiments, the anti-PTPRA inhibitory nucleic acid has at least 50% sequence identity to a contiguous sequence of SEQ ID NO:1, SEQ ID NO:2 or SEQ ID NO:3 spanning at least 20 nucleotides.

In embodiments, the anti-PTPRA inhibitory nucleic acid has at least 60% sequence identity to a contiguous sequence of SEQ ID NO:1, SEQ ID NO:2 or SEQ ID NO:3 spanning at least 20 nucleotides.

In embodiments, the anti-PTPRA inhibitory nucleic acid has at least 70% sequence identity to a contiguous sequence of SEQ ID NO:1, SEQ ID NO:2 or SEQ ID NO:3 spanning at least 20 nucleotides.

In embodiments, the anti-PTPRA inhibitory nucleic acid has at least 80% sequence identity to a contiguous sequence of SEQ ID NO:1, SEQ ID NO:2 or SEQ ID NO:3 spanning at least 20 nucleotides.

In embodiments, the anti-PTPRA inhibitory nucleic acid has at least 90% sequence identity to a contiguous sequence of SEQ ID NO:1, SEQ ID NO:2 or SEQ ID NO:3 spanning at least 20 nucleotides.

In embodiments, the anti-PTPRA inhibitory nucleic acid has at least 50% sequence identity to a contiguous sequence of SEQ ID NO:1, SEQ ID NO:2 or SEQ ID NO:3 spanning at least 25 nucleotides.

In embodiments, the anti-PTPRA inhibitory nucleic acid has at least 60% sequence identity to a contiguous sequence of SEQ ID NO:1, SEQ ID NO:2 or SEQ ID NO:3 spanning at least 25 nucleotides.

In embodiments, the anti-PTPRA inhibitory nucleic acid has at least 70% sequence identity to a contiguous sequence of SEQ ID NO:1, SEQ ID NO:2 or SEQ ID NO:3 spanning at least 25 nucleotides.

In embodiments, the anti-PTPRA inhibitory nucleic acid has at least 80% sequence identity to a contiguous sequence of SEQ ID NO:1, SEQ ID NO:2 or SEQ ID NO:3 spanning at least 25 nucleotides.

In embodiments, the anti-PTPRA inhibitory nucleic acid has at least 90% sequence identity to a contiguous sequence of SEQ ID NO:1, SEQ ID NO:2 or SEQ ID NO:3 at least 25 nucleotides.

In embodiments, the anti-PTPRA inhibitory nucleic acid has at least 50% sequence identity to a contiguous sequence of SEQ ID NO:1, SEQ ID NO:2 or SEQ ID NO:3 spanning at least 30 nucleotides.

In embodiments, the anti-PTPRA inhibitory nucleic acid has at least 60% sequence identity to a contiguous sequence of SEQ ID NO:1, SEQ ID NO:2 or SEQ ID NO:3 spanning at least 30 nucleotides.

In embodiments, the anti-PTPRA inhibitory nucleic acid has at least 70% sequence identity to a contiguous sequence of SEQ ID NO:1, SEQ ID NO:2 or SEQ ID NO:3 spanning at least 30 nucleotides.

In embodiments, the anti-PTPRA inhibitory nucleic acid has at least 80% sequence identity to a contiguous sequence of SEQ ID NO:1, SEQ ID NO:2 or SEQ ID NO:3 spanning at least 30 nucleotides.

In embodiments, the anti-PTPRA inhibitory nucleic acid has at least 90% sequence identity to a contiguous sequence of SEQ ID NO:1, SEQ ID NO:2 or SEQ ID NO:3 spanning at least 30 nucleotides.

In embodiments, the PTPRA antagonist is an anti-PTPRA inhibitory nucleic acid, wherein the anti-PTPRA inhibitory nucleic acid has at least 90% sequence identity to an at least 10 nucleotide contiguous sequence of SEQ ID NO: 1, SEQ ID NO:2, SEQ ID NO:3 or a complementary sequence thereof.

In embodiments, the PTPRA antagonist is a PTPRA ligand mimetic, wherein the anti-PTPRA ligand mimetic is a peptide or a small chemical molecule.

III. Pharmaceutical Compositions

In another aspect, there is provided a pharmaceutical composition including a PTPRA antagonist and a pharmaceutically acceptable excipient.

In embodiments, the pharmaceutical composition is for treating an individual who has a disease by administering to the individual a pharmaceutical composition including a therapeutically effective amount of a PTPRA antagonist and a pharmaceutically acceptable excipient. In embodiments, the pharmaceutical composition is for treating an individual who may be at risk of developing a disease by administering to the individual a pharmaceutical composition including a therapeutically effective amount of a PTPRA antagonist and a pharmaceutically acceptable excipient. In embodiments, the disease is an autoimmune disease or disorder, cancer, an infectious disease (e.g. viral, bacterial, parasitic, etc.), an obesity associated disease, a metabolic disease or disorder, an inflammatory disease, an immune disease or disorder, or a traumatic injury. In embodiments, the disease is an inflammatory autoimmune disease (IAD). In embodiments, the disease is a disease associated with a patient's joints. In a certain embodiment, the inflammatory autoimmune disease is rheumatoid arthritis. In embodiments, increased expression of one or more RPTPs is associated with a disease or a risk of developing the disease. In embodiments, decreased expression of one or more RPTPs is associated with a disease or a risk of developing the disease. In embodiments, the increased expression of a first RPTP and the decreased expression of a second RPTP are associated with a disease or a risk of developing the disease.

The PTPRA antagonist may be an anti-PTPRA antibody. In embodiments, the PTPRA antagonist is an anti-PTPRA inhibitory nucleic acid. In embodiments, the anti-PTPRA inhibitory nucleic acid is an anti-PTPRA RNAi molecule. In embodiments, the anti-PTPR inhibitory nucleic acid is an antisense nucleic acid such as anti-PTPRA antisense nucleic acid. In embodiments, the PTPRA antagonist is a PTPRA ligand mimetic. In embodiments, the PTPRA ligand mimetic is a peptide or a small chemical molecule. In embodiments, the PTPRA ligand mimetic is an allosteric inhibitor. In embodiments, the PTPRA antagonist is an anti-PTPRA antisense nucleic acid. In embodiments, the PTPRA antagonist is anti-PTPRA antisense nucleic acid.

In embodiments, the pharmaceutical composition is useful for treating an individual who has or may be at risk of developing an inflammatory autoimmune disease. In embodiments, the pharmaceutical compositions are useful for treating an individual who has an inflammatory autoimmune disease by administering to the individual a pharmaceutical composition including a therapeutically effective amount of a PTPRA antagonist and a pharmaceutically acceptable excipient. In embodiments, the pharmaceutical compositions are for treating an individual who may be at risk of developing an autoimmune disease by administering to the individual a pharmaceutical composition including a therapeutically effective amount of a PTPRA antagonist and a pharmaceutically acceptable excipient. In embodiments, the inflammatory autoimmune disease is an arthritis. In embodiments, the autoimmune disease is fibroblast mediated disease, arthritis, osteoarthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome,vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, scleroderma, systemic sclerosis, or allergic asthma. In embodiments, the autoimmune disease is rheumatoid arthritis.

The compositions disclosed herein can be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Administration can be local, e.g., to the joint or systemic.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

There are provided methods of treating, preventing, and/or ameliorating an autoimmune disorder in a subject in need thereof, optionally based on the diagnostic and predictive methods described herein. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Administration of a composition for ameliorating the autoimmune disease can be a systemic or localized administration. For example, treating a subject having an autoimmune disorder can include administering an oral or injectable form of PTPRA antagonist on a daily WO 2016/040510 PCT/US2015/049228 basis or otherwise regular schedule. In embodiments, the treatment is only on an as-needed basis, e.g., upon appearance of autoimmune disease symptoms.

In embodiments, the PTPRA antagonist is an anti-PTPRA antibody, an anti-PTPRA inhibitory nucleic acid or a PTPRA ligand mimetic. In embodiments, the PTPRA antagonist is an anti-PTPRA antibody. In embodiments, the PTPRA antagonist is an anti-PTPRA inhibitory nucleic acid. In embodiments, the PTPRA antagonist is a PTPRA ligand mimetic.

In embodiments, the PTPRA antagonist is an anti-PTPRA extracellular antibody.

In embodiments, the anti-PTPRA antibody is an anti-PTPRA dimer inhibiting antibody or an anti-PTPRA dimerizing antibody.

In embodiments, the PTPRA antagonist is an anti-PTPRA inhibitory nucleic acid, wherein the anti-PTPRA inhibitory nucleic acid as set forth above, including all embodiments thereof.

In embodiments, the PTPRA antagonist is a PTPRA ligand mimetic, wherein the anti-PTPRA ligand mimetic is a peptide or a small chemical molecule.

Any appropriate element disclosed in one aspect or embodiment of a method or composition disclosed herein is equally applicable to any other aspect or embodiment of a method or composition. For example, the therapeutic agents set forth in the description of the pharmaceutical compositions provided herein are equally applicable to the methods of treatment and vice versa.

A number of embodiments of the invention have been described. Nevertheless, it will be understood that various modifications may be made without departing from the spirit and scope of the invention. Accordingly, the following examples are intended to illustrate but not limit the scope of the invention described in the claims.

EXAMPLES

Example 1

Material and Methods

Antibodies and Reagents

The rabbit anti-RPTPα antibody was previously described (14). Other primary antibodies were purchased from Cell Signaling Technology (Danvers, Mass.) and secondary antibodies from GE Healthcare Life Sciences (Pittsburgh, Pa.). TNFα, IL-1β and PDGF-BB were purchased from eBioscience (San Diego, Calif.). The FAK inhibitor PF573228 was purchased from EMD Millipore (Billerca, Mass.). The AKT inhibitor MK2206 was purchased from SelleckChem (Houston, Tex.). Unless specified, other reagents were purchased from Sigma-Aldrich (St. Louis, Mo.).

Immunohistochemistry (IHC) of Synovial Tissue

Figure 10A:
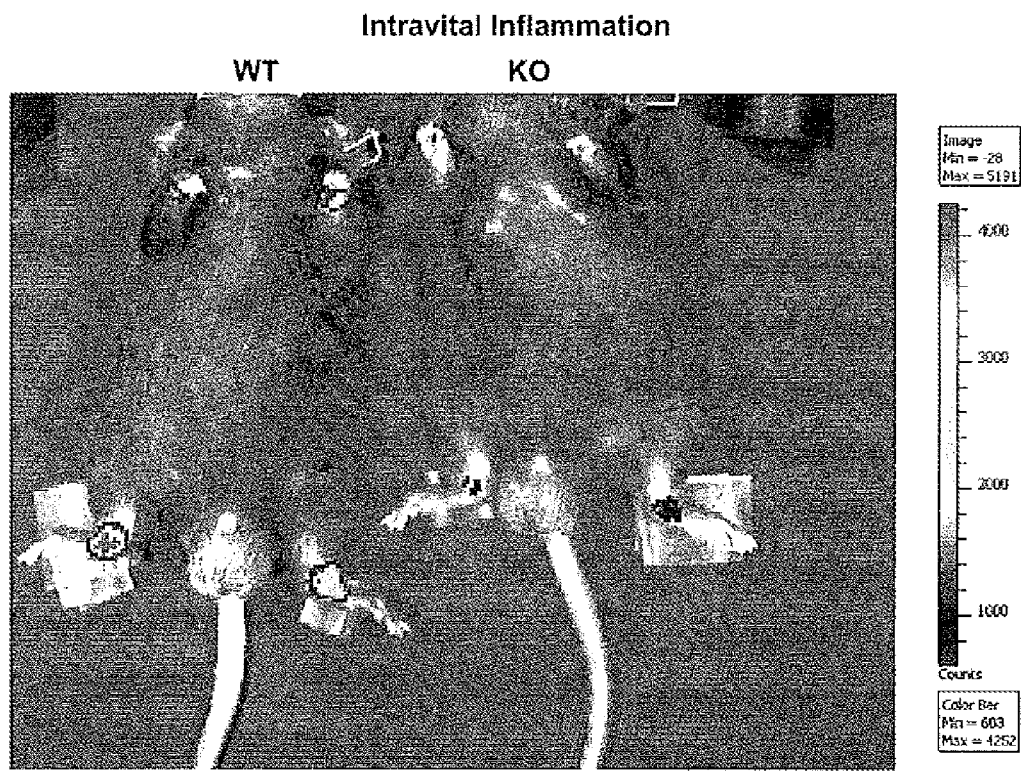
FIGS. 10A-10C: Ptpra KO mice are protected from inflammation during K/BxN passive transfer arthritis.
Figure 10B:
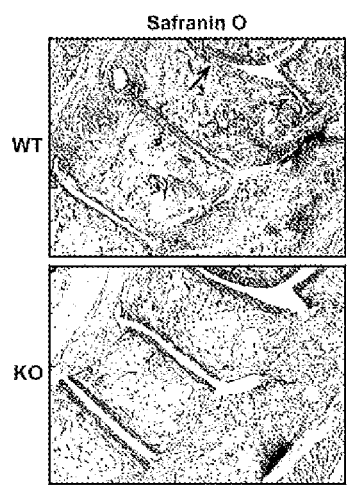
Figure 10C:
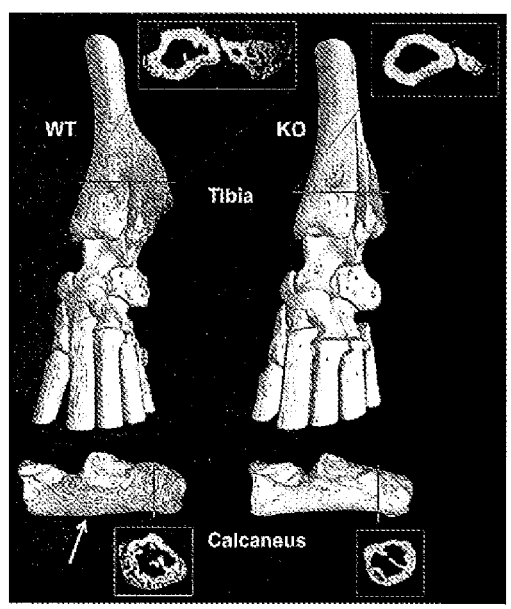

The anti-RPTPα antibody was optimized for IHC using arthritic ankle sections of WT and PTPRA KO mice observed in FIGS. 10A-10C. Paraffin embedded slides of human RA synovial tissues were obtained from the UCSD Clinical and Translational Research Institute (CTRI) Biorepository. Slides were deparaffinated, rehydrated and pre-treated for 10 minutes with boiling citrate antigen retrieval buffer (1.9 mM citric acid, 10 mM Tris-sodium citrate pH 6.0), and treated with 3% $H_2O_2$ for 10 minutes. Slides were blocked with 5% goat serum for 1 hour at room temperature, and then incubated with rabbit anti-RPTPα antibody or control rabbit IgG (1:100 in 5% bovine serum albumin [BSA]) overnight at 4° C. Slides were washed and incubated with SignalStain Boost IHC Detection reagent (HRP, rabbit) (Cell Signaling Technologies) for 30 minutes, incubated for 5 min with 3,3'-diaminobenzidine substrate (Sigma-Aldrich), and counterstained with hematoxylin. Slide images were obtained using an Eclipse 80i microscope (Nikon, Melville, N.Y.).

Preparation of FLS

FLS were obtained from the UCSD CTRI Biorepository. Each line was previously obtained from discarded synovial tissue of a different patient with RA at the time of synovectomy, as described previously (21). The diagnosis of RA conformed to American College of Rheumatology 1987 revised criteria(22). FLS were cultured in DMEM (Mediatech, Manassas, Va.) with 10% fetal bovine serum (FBS, Omega Scientific, Tarzana, Calif.), 2 mM L-glutamine, 50 mg/mL gentamicin, 100 units/ml of penicillin and 100 mg/ml streptomycin (Life Technologies, Carlsbad, Calif.) at 37° C. in a humidified 5% CO2 atmosphere. For all experiments, FLS were used between passages 4-10, and cells were synchronized in 0.1% FBS (serum-starvation media) for 48 hours prior to analysis or functional assays.

Quantitative Polymerase Chain Reaction (qPCR)

RNA was extracted using RNeasy Kits (Qiagen, Valencia, Calif.) or Trizol (Life Technologies). For lysis of FLS, adherent cells were first washed in PBS and then lysed in the culture plate. cDNA was synthesized using the SuperScript® III First-Strand Synthesis SuperMix (Life Technologies). qPCR was performed using a Roche Lightcycler 480 (Indianapolis, Ind.), with primer assays from SABiosciences/Qiagen. Reactions were measured in triplicate and data was normalized to the expression levels of the housekeeping gene glyceraldehyde 3-phosphate dehydrogenase (GAPDH) or RNA Polymerase II (RPII) (23).

FLS Treatment with Cell-Permeable Antisense Oligonucleotide (PMO)

FLS were treated with 2.5 uM PMO (Gene Tools, Philomath, OR) for 7 days. PMO was replaced in fresh culture medium after 3 days and in serum-starvation medium after 5 days.

Enzyme-Linked Immunosorbent Assay (ELISA)

Secreted human IL-6 and chemokine (C-X-C motif) ligand 10 (CXCL10) were measured using ELISAs from Biolegend (San Diego, Calif.).

Transwell Invasion Assay

In vitro invasion assays were performed in transwell systems as described elsewhere (24,25). Following treatment with PMO, equal numbers of live RA FLS were re-suspended in assay media (DMEM with 0.5% BSA) and allowed to invade through BD BioCoat™ GFR Matrigel™ chambers in response to 50 ng/ml PDGF-BB for 48 hr. Cells were pre-stained with 2 μM CellTracker Green™ or stained post-invasion with 2 uM Hoechst (Life Technologies) for 30 minutes at room temperature. Fluorescence of invading cells on each membrane was visualized using an Eclipse 80i microscope. Images were acquired from 4 non-overlapping fields per membrane, and invading cells in each field were counted using ImageJ software. Each experiment included 3-4 membranes per sample.

Transwell Migration Assay

Transwell migration assays were similarly performed. Following treatment with PMO, equal numbers of live RA FLS were allowed to migrate through uncoated transwell chambers in response to 5% FBS for 24 hours. Each experiment included 3-4 membranes per sample.

Survival and Apoptosis Assay

Following treatment with PMO, RA FLS were washed and incubated for an additional 24 hoursr in serum-starvation media. Adherent and non-adherent cells were collected and stained with Annexin V-Alexa Fluor® 647 and propidium iodide (PI) according to the manufacturer's instructions (Biolegend, San Diego, Calif.). Cell fluorescence was assessed by FACS using a BD LSR-II (BD Biosciences), and counts and percentages of live (Annexin V−PI−), early apoptotic (Annexin V+PI−), or late apoptotic/necrotic (Annexin V+PI+) cells were obtained. Data was analyzed for statistical significance using the Chi-square test for independence.

Spreading and Adhesion Assay

Following treatment with PMO, equal numbers of live RA FLS were re-suspended in FLS medium containing 5% FBS and allowed to adhere onto coverslips coated with 20

µg/ml fibronectin (FN) at 37° C. for 15, 30 and 60 minutes. Cells were fixed in 4% para-formaldehyde for 5 minutes, permeabilized in 0.2% Triton X-100 for 2 minutes, and stained with 5 U/ml Alexa Fluor® 568 (AF 568)-conjugated phalloidin and 2 µg/ml Hoechst for 20 minutes (Life Technologies). Samples were imaged with an Olympus FV10i Laser Scanning Confocal Microscope (Olympus, Center Valley, Pa.). Using the FV10i acquisition software, each coverslip was separated into four nine-paneled mega-images. Each panel (1024×1024) was acquired with a 10× objective and then stitched together, through a 10% overlap, with the Olympus FluoView 1000 imaging software. Total cell number and cell areas for each panel were calculated using Image Pro Analyzer software (Media Cybernetics, Rockville, Md.).

Cell Lysis for Western Blotting (WB)

Adherent cells were washed in PBS and then lysed in the culture plate in RIPA buffer (25 mM Tris-HCl pH 7.6, 150 mM NaCl, 1% NP-40, 1% sodium deoxycholate, 0.1% SDS) containing 1 mM phenylmethanesulfonyl fluoride, 10 ng/ml aprotinin, 10 µg/ml leupeptin, 10 µg/ml soybean trypsin inhibitor, 10 mM sodium orthovanadate, 5 mM sodium fluoride and 2 mM sodium pyrophosphate. Protein concentration of cell lysates was determined using the Pierce BCA Protein Assay Kit (Thermo Scientific, Rockford, Ill.).

Mice

Animal experiments were conducted in accordance with La Jolla Institute for Allergy and Immunology (LJI) Institutional Animal Care and Use Committee-approved protocol (#AP140-NB4). PTPRA KO mice were generated as previously described (26). C57BL/6 KRN mice were provided by Dr. Christophe Benoist (Harvard Medical School) and were crossed with NOD mice (Jackson Laboratories, Bar Harbor, Minn.) to obtain arthritic offspring (K/BxN mice) whose sera was pooled for use in the K/BxN passive serum transfer arthritis model (27). Congenic CD45.1 C57BL/6 mice were purchased from Taconic Biosciences (Hudson, N.Y.).

K/BxN Passive Serum Transfer Arthritis Model

Arthritis was induced in 8 week-old mice by intraperitoneal (i.p.) injection of 200 µL pooled sera from K/BxN mice. Every 2 days, ankle thickness was measured using a digital caliper(27).

Reciprocal Bone-Marrow Transplantation

Male recipient mice were lethally irradiated with 2 doses of 550 rads and administered bone-marrow from male donor mice. WT congenic CD45.1 mice were administered bone-marrow cells from WT or PTPRA KO CD45.2 mice, and WT or PTPRA KO mice were administered bone-marrow cells from WT congenic CD45.1 mice. KBxN pooled sera was administered to induce arthritis 10-11 weeks post-irradiation. Percentage of engrafted cells in WT recipients reconstituted with KO bone-marrow and in KO recipients reconstituted with WT bone-marrow was >90%.

Assessment of Inflammation with an Intravital Probe

The Xenolight Rediject Inflammation Probe (PerkinElmer, Waltham, Mass.) is an intravital luminescent dye that penetrates phagocytic cells and enables visualization of joint infiltration. Probe was administered to mice 7 days after arthritis induction by i.p. injection according to the manufacturer's instructions. Joint inflammation was quantified using the Xenogen IVIS Spectrum in vivo Imaging System (Perkin Elmer).

Histological Analysis of Arthritic Joints

Hind paws were fixed in 10% neutral-buffered formalin, decalcified and embedded in paraffin. Sections were prepared from the tissue blocks and stained with H&E and Safranin-O/Fast Green/Hematoxylin (HistoTox, Boulder Colo.). Histopathological scoring was performed as previously described(28). Joints were given scores of 0-4 for bone erosion: 0=normal; 1=minimal (small areas of erosion, not readily apparent on low magnification); 2=mild (more numerous areas of erosion, not readily apparent on low magnification, in trabecular or cortical bone); 3=moderate (obvious erosion of trabecular and cortical bone, without full-thickness cortex defects; loss of some trabeculae; lesions apparent on low magnification); and 4=marked (full-thickness defects in the cortical bone and marked trabecular bone loss). Cartilage depletion was identified by diminished Safranin-O staining of the matrix and was scored on a scale of 0-4: 0=no cartilage destruction (full Safranin-O staining); 1=localized cartilage erosions; 2=more extended cartilage erosions; 3=severe cartilage erosions; and 4=depletion of entire cartilage. Histologic analyses were performed in a blinded manner by 2 independent operators.

Joint Extravasation Assay

Mice were injected retro-orbitally with AngioSense-680 Probe according to the manufacturer's instructions (PerkinElmer), and after 5 min were injected i.p. with arthritogenic K/BxN sera. After 1 hour, joint fluorescence was quantified using the Xenogen IVIS Spectrum.

Statistical Analysis

The two-way analysis of variance, Mann-Whitney test, Wilcoxon matched-pairs signed rank test, and Chi-square test for independence were performed using GraphPad Prism software. A comparison was considered significant if p was <0.05.

Example 2

RPTPα is Expressed in Fibroblasts from the RA Synovium

Figure 11A:
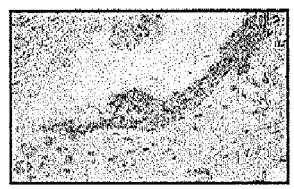
Figure 11A:
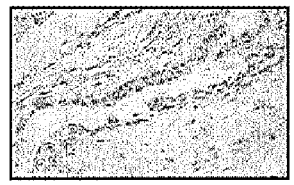
Figure 11B:
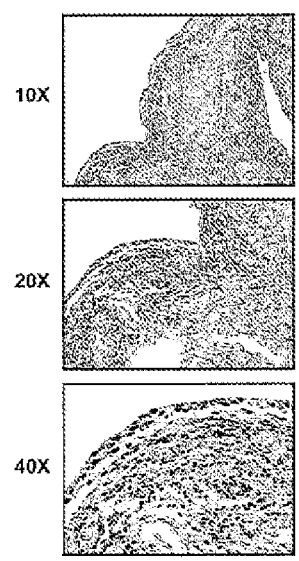
FIG. 11B: Immunohistochemical staining of RA synovial section using anti-RPTPα antibody.

Applicants previously reported high expression of PTPRA in cultured RA FLS (11). Here, IHC of human RA synovial sections revealed prominent RPTPα expression in the synovial intimal lining, as depicted in FIG. 1A and FIGS. 11A-11B. Applicants found that stimulation of RA FLS with TNF and IL-1β had no effect on PTPRA.

Example 3

RPTPα Promotes Responsiveness of FLS to Inflammatory Cytokine Stimulation

Figure 1B:
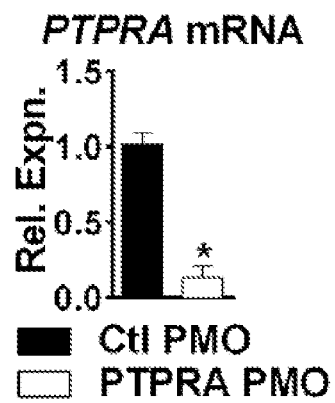
Figure 1C:
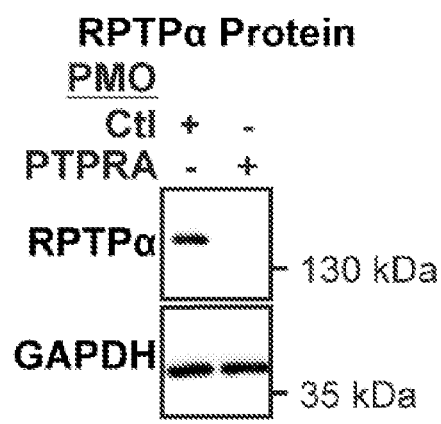
Figure 1D:
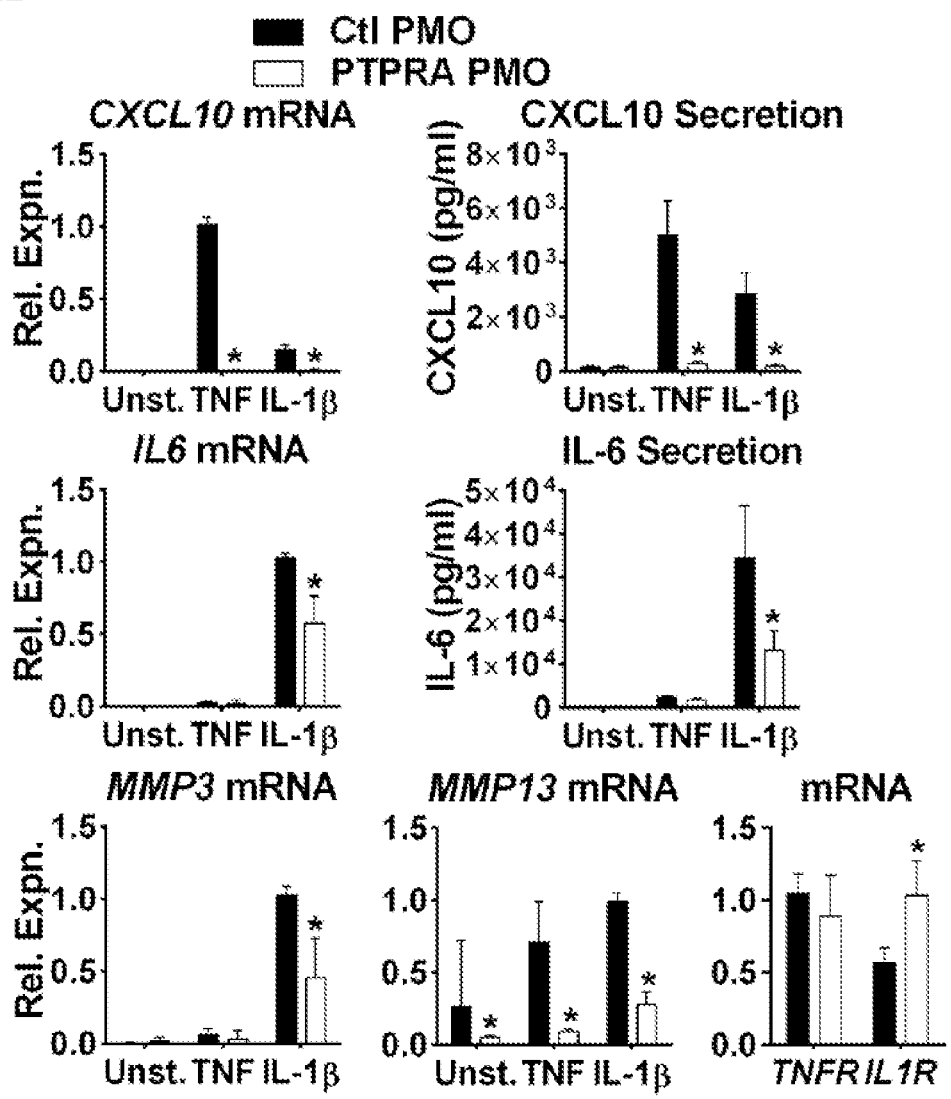
Figure 8A:
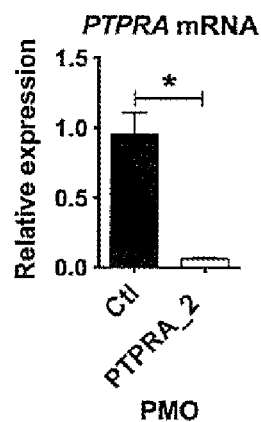
FIGS. 8A-8B: RPTPα promotes TNF and IL-1 signaling in RA FLS.
Figure 8B:
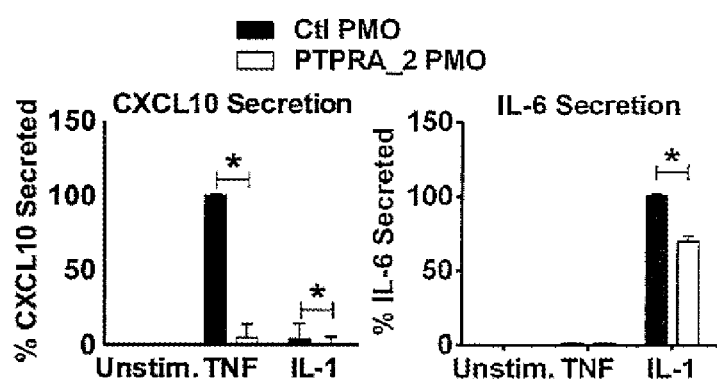

Applicants subjected RA FLS to RPTPα knockdown with cell-permeable antisense oligonucleotide (PMO), shown in FIGS. 1B-1C, to test the effects of RPTPα deficiencies on the response of RA FLS to TNF and IL-1β stimulation. Treatment with PTPRA PMO significantly reduced RA FLS production of CXCL10 and MMP13 in response to TNF, and significantly reduced RA FLS production of IL6, CXCL10, MMP3 and MMP13 in response to IL-1β, as seen in FIG. 1D. Applicants assessed whether these effects were due to down-regulation of TNF receptor (TNFRSF1A) or IL-1β receptor (IL1R) expression, to which there was no effect on expression of TNFRSF1A, however PTPRA PMO increased expression of IL1R, which is also seen in FIG. 1D. The effect on CXCL10 and IL-6 was further confirmed by treatment of RA FLS with a second PTPRA-targeted PMO of a different sequence, shown in FIGS. 8A-8B. Taken together, the data suggests that RPTPα promotes production of pro-inflammatory and pro-invasive mediators by RA FLS in response to inflammatory cytokines. While a role for RPTPα in the regulation of IL-1β signaling has been previously reported (29-31), this is the first report of a role for RPTPα in TNF signaling.

Example 4

RPTPα Promotes RA FLS Invasiveness

Figure 2A:
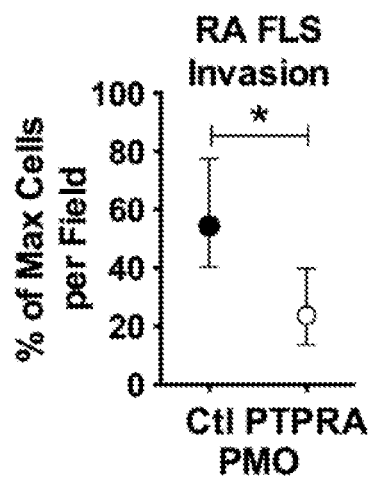
FIGS. 2A-2D. RPTPα promotes RA FLS invasiveness.
Figure 2B:
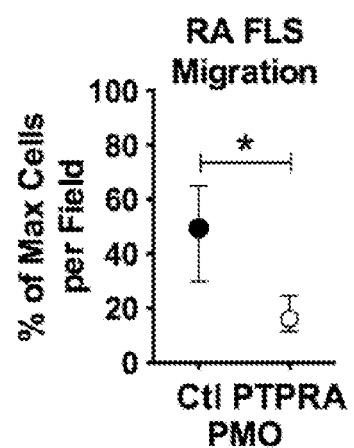
Figure 2C:
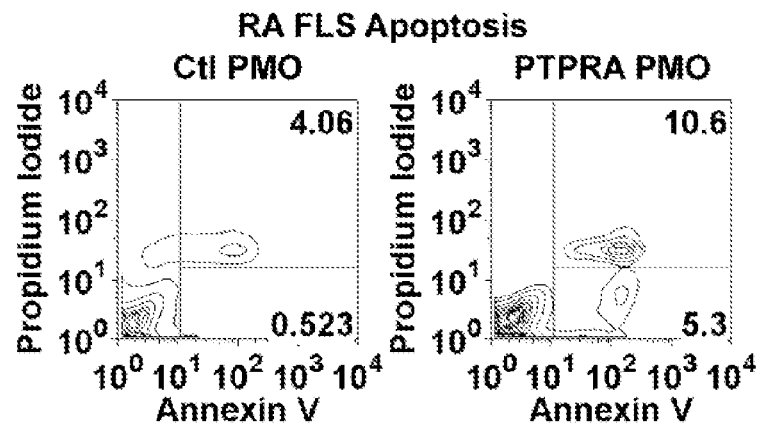
Figure 2D:
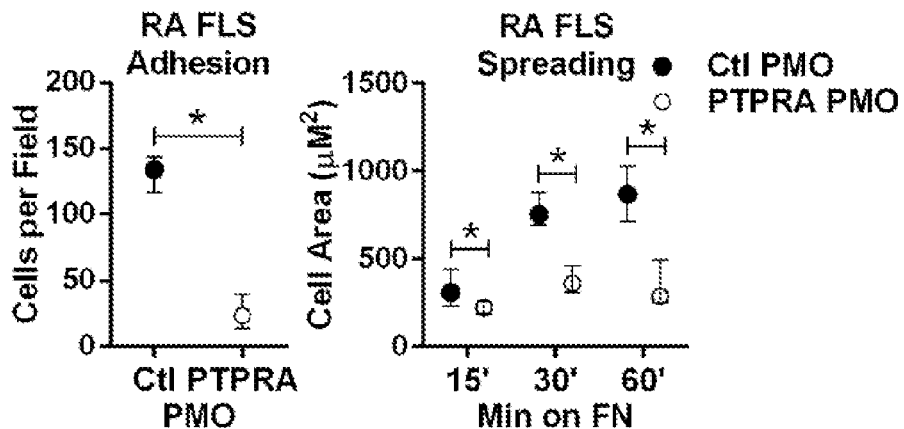

RA FLS invasiveness ex vivo was shown to correlate with radiographic damage during RA progression (25). Applicants subjected PMO-treated RA FLS to transwell invasion assays through Matrigel in response to PDGF, a highly expressed promoter of FLS invasiveness in the RA synovium (4). RA FLS treated with PTPRA PMO, compared to control non-targeting PMO-treated cells, were significantly less invasive in response to PDGF, as shown in FIG. 2A; median and IQR % max cells per field 54.4 and 40.3-77.5 for Ctl PMO; 23.8 and 13.7-40.0 for PTPRA PMO, p<0.05. PTPRA PMO-treated cells showed significantly reduced migration in a transwell assay in response to 5% FBS, as reported in FIG. 2B; median and IQR % max cells per field 49.4 and 29.8-64.9 for Ctl PMO; 16.1 and 11.4-24.5 for PTPRA PMO. This could be due to increased cell death or to reduced cytoskeletal reorganization following RPTPα knockdown. To test this hypothesis, assays of PTPRA PMO on cell apoptosis and necrosis, and on cell spreading were tested. RA FLS treated with PTPRA PMO showed significantly increased apoptosis compared to control-treated cells in sera-starvation media or in the presence of PDGF, observed in FIG. 2C. Additionally, live PTPRA PMO-treated cells were less adherent to, and displayed impaired spreading on, fibronectin-coated coverslips shown in FIG. 2D. Taken together, this data strongly supports the role for RPTPα in promoting RA FLS survival and growth factor-dependent cytoskeletal reorganization, migration and invasiveness.

Example 5

RPTPα Promotes RA FLS Aggressiveness Through Control of SRC and FAK Activation

Figure 3A:
FIGS. 3A-3D. RPTPα promotes RA FLS signaling downstream SRC.
Figure 3B:
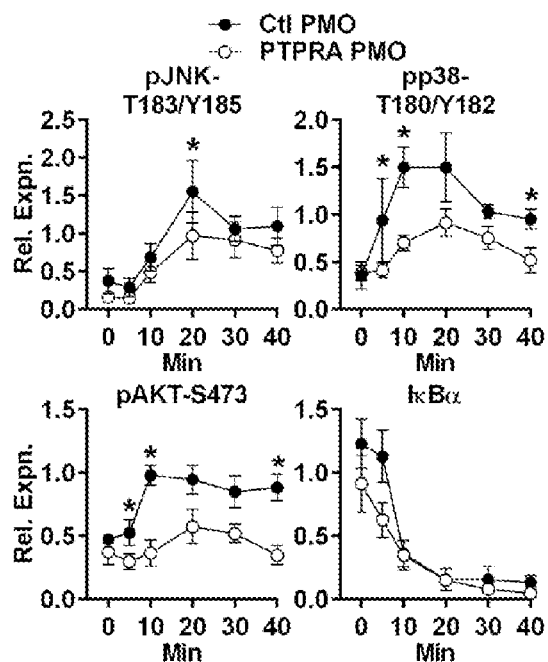
Figure 3C:
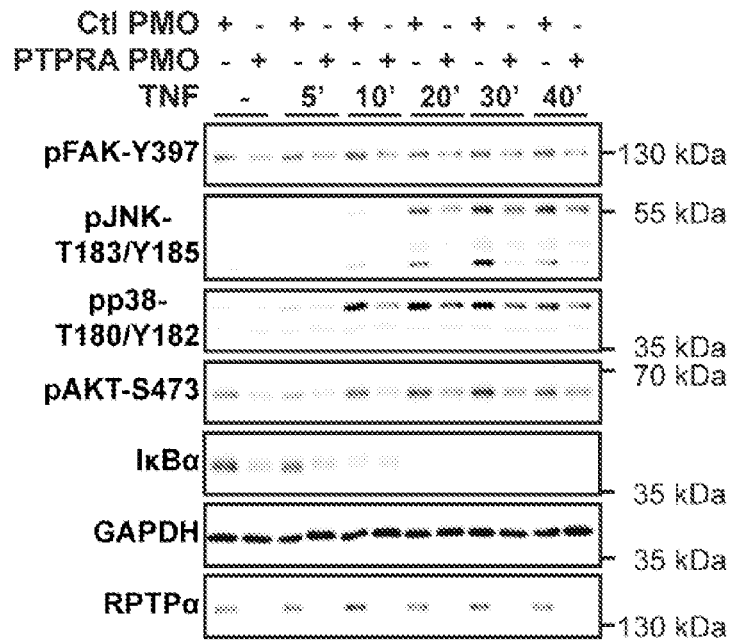
Figure 3D:
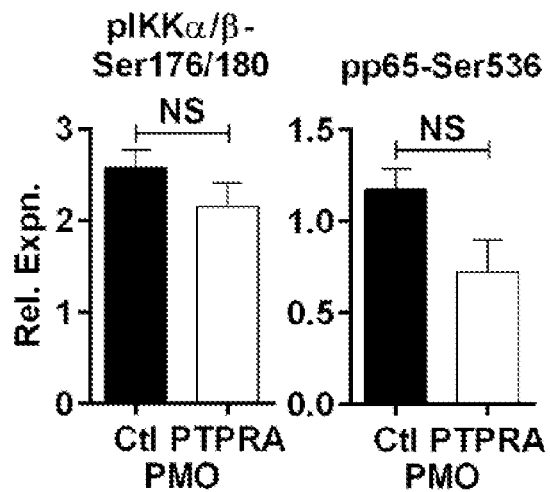

The inhibitory SRC tyrosine residue (Y527) was identified as the physiological substrate of RPTPα in multiple cell types (14, 16). Dephosphorylation of SRC-Y527 enhances SRC activation, leading to tyrosine phosphorylation of FAK-Y397—a substrate of SRC(7)- and other SRC substrates. In RA FLS, phospho-SRC-Y527 is constitutive and not induced by TNF or IL-1β stimulation. Applicants assessed whether RPTPα knockdown in RA FLS influences basal SRC-Y527 phosphorylation levels, and found that RPTPα knockdown increased phosphorylation of SRC-Y527 in resting RA FLS, displayed in FIG. 3A. While testing whether RPTPα knockdown affected signaling downstream SRC in RA FLS, FAK-Y397 was found constitutively phosphorylated in RA FLS. Phospho-FAK-Y397 was unaffected by TNF and IL-1β stimulation and its phosphorylation was reduced by RPTPα knockdown, as seen in FIG. 3C. As FAK promotes activation of mitogen-activated protein kinases (MAPKs) (7), and is critical for c-Jun N-terminal kinase (JNK) activation in RA FLS (32), it is important to assess if RPTPα knockdown affects TNF- and IL-1β-induced activation of the JNK and p38 MAPKs. Applicants found RPTPα knockdown impaired TNF- and IL-1β-stimulated phosphorylation of the activation motif of JNK (T183/Y185) and also p38-T180/Y182, reported in FIG. 3B and FIG. 3C. Applicants also examined whether RPTPα promoted activation of the AKT and NF-κB signaling pathways, which are activated by inflammatory cytokine stimulation in RA FLS (4). As shown in FIGS. 3B-3C, PTPRA PMO treatment reduced TNF- and IL-1β stimulated phosphorylation of AKT-S473. Interestingly, PTPRA PMO treatment caused a modest decrease in the levels of IKBα protein in resting RA FLS. Stimulation of cells with TNF or IL-1β, however caused degradation of IκBα protein in both Ctl and PTPRA PMO-treated cells, and following 10 minutes post-stimulation the levels of IκBα were similar between Ctl and PTPRA PMO-treated cells, seen in FIG. 3B and FIG. 3C. The trend of decreased basal levels of IκBα in PTPRA PMO-treated cells was not accompanied by increased basal activation of the NFκB pathway, but rather a non-significant trend towards decreased basal phosphorylation of IκB kinase (IKK)-αβ on Ser176/180 and NFκB subunit p65 on Ser536, as reported in FIG. 3D. Additionally, proteolytic processing of NFκB subunits p100 and p105—as assessed by the ratio of p52:p100 or p50:p105, respectively—in basal conditions is unaffected by PTPRA knockdown.

Figure 4A:
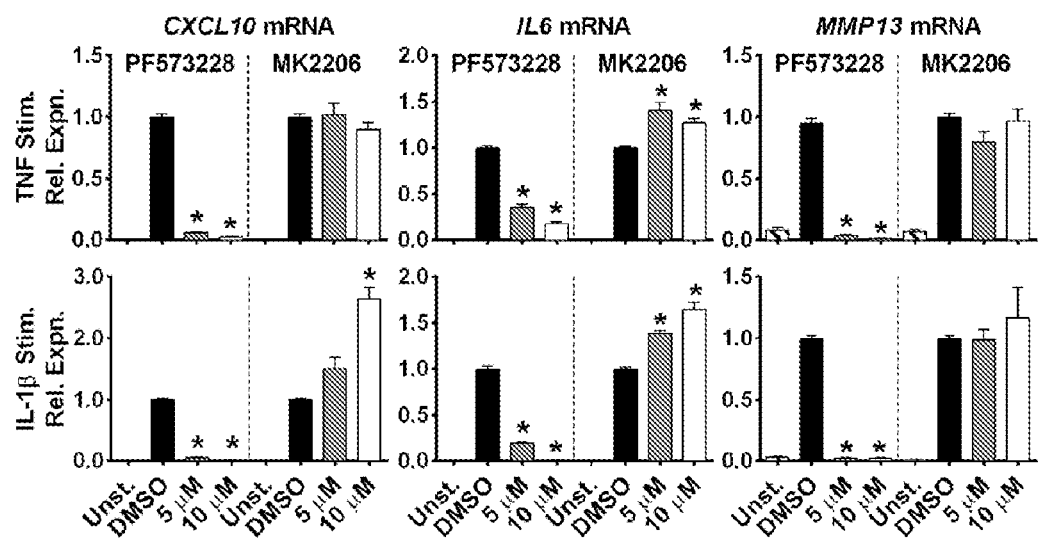
FIGS. 4A-4B. FAK inhibition impairs activation of JNK and TNF and IL-1β-induced gene expression in RA FLS.
Figure 4B:
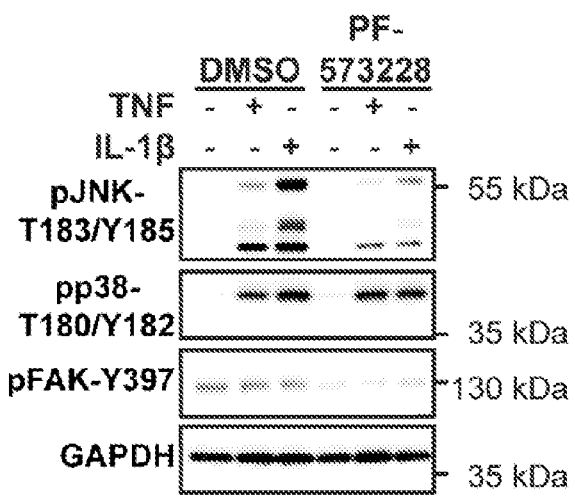
Figure 9:
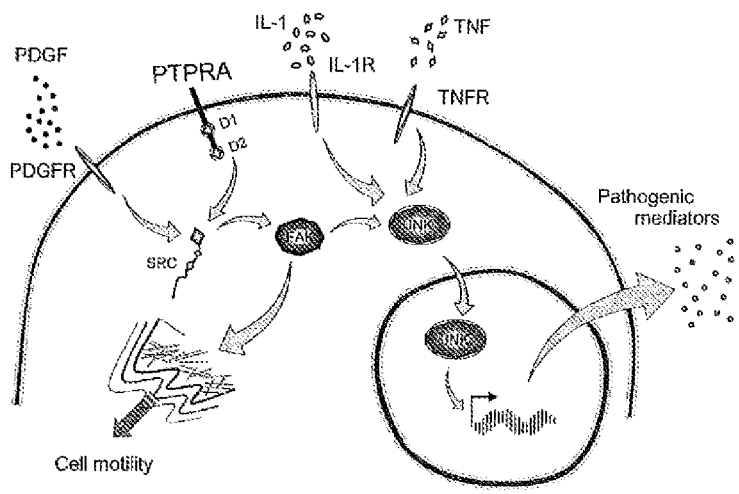
FIG. 9: Working model of the function of RPTPα in FLS signaling. RPTPα dephosphorylates and activates the kinase SRC, which in turn promotes activation of the FAK pathway, leading to increased cell migration downstream the PDGF receptor (PDGFR). The FAK pathway also promotes TNF- and IL-1-induced pro-inflammatory output in part through activation of the MAPK JNK.

Using pharmacological inhibitors, applicants tested whether FAK or AKT play essential roles in RA FLS induction of gene expression in response to TNF and IL-1. Similar to the effect of RPTPα knockdown, recall from FIG. 1D, treatment of RA FLS with the FAK inhibitor PF573228 led to significantly decreased TNF- and IL-1-induced production of CXCL10, IL6 and MMP13, as seen in FIG. 4A. On the contrary, treatment with the AKT inhibitor MK2206 did not dampen expression of any these genes, but rather increased expression of IL6 and IL-1β-induced expression of CXCL10, also seen in FIG. 4A. Applicants confirmed that treatment of RA FLS with PF573228 does not cause death of RA FLS at the concentrations used in these experiments. Treatment of RA FLS with PF573228 impaired FAK-Y397 phosphorylation and TNF- and IL-1β-induced phosphorylation of JNK-T183/Y185, displayed in FIG. 4B, but had no effect on p38-T180/Y185 phosphorylation. These findings strongly suggest that RPTPα promotes TNF- and IL-1β-stimulated production of CXCL10, IL-6 and MMP-13 through a SRC-FAK-JNK signaling pathway. RPTPα also likely promotes other signaling pathways in RA FLS—such as the AKT and p38 pathways—that are independent of FAK. Taken together, these data suggest a model illustrated in FIG. 9 whereby RPTPα mediates RA FLS aggressiveness by promoting constitutive activation of SRC and FAK, leading to enhanced FLS survival, increased production of critical mediators of arthritis in response to TNF and IL-1β, and promotion of motility and invasiveness in response to PDGF.

Example 6

Figure 5A:
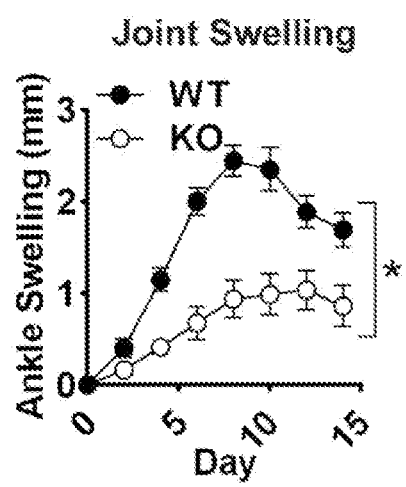
FIGS. 5A-5C. Ptpra KO mice are resistant to K/BxN serum transfer arthritis. WT and Ptpra KO littermate mice were administered 200 µl K/BxN sera at 8 weeks of age.
Figure 5B:
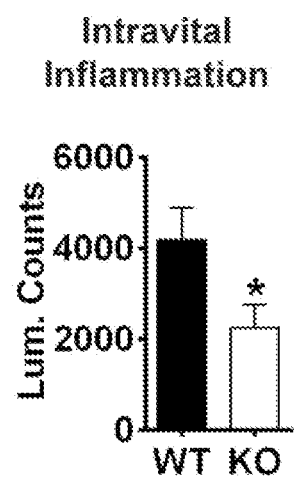
Figure 5C:
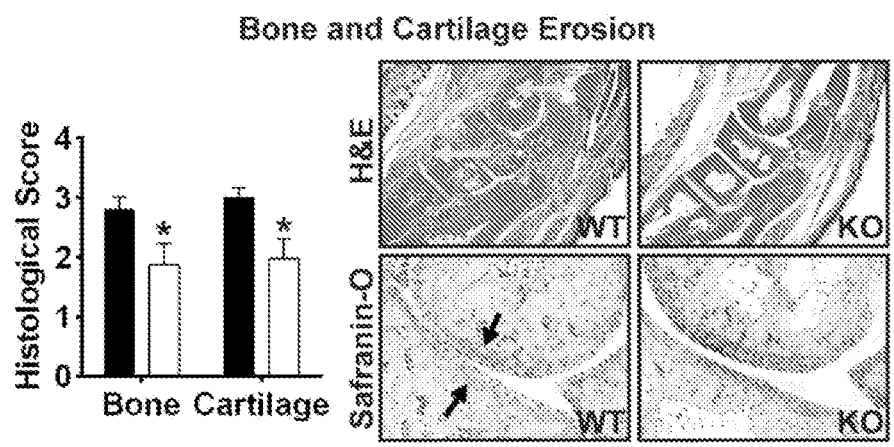
Figure 7A:
FIGS. 7A-7C. Ptpra KO mice are protected from K/BxN passive transfer arthritis, which is dependent upon radioresistant cells. Histological analysis of ankles stained with H&E or Safranin O at the end of the disease course.
Figure 7B:
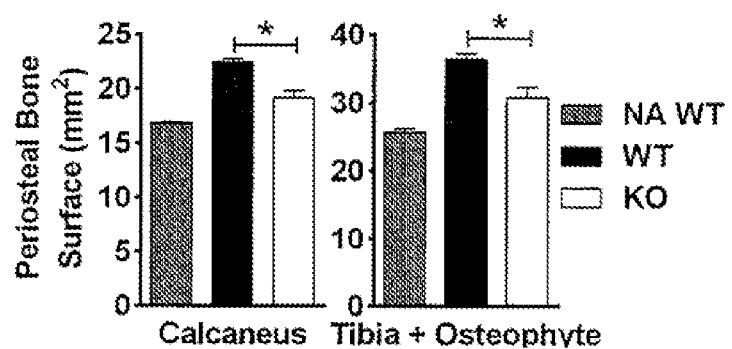
Figure 7C:
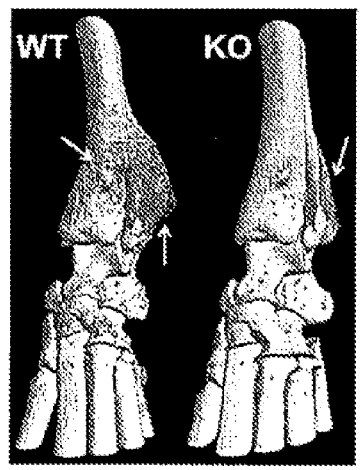

PTPRA KO Mice are Resistant to K/BxN Passive Transfer Arthritis Through an Effect on Radioresistant Cells Applicants subjected wild-type (WT) and PTPRA KO mice to the FLS-dependent K/BxN serum transfer model of inflammatory arthritis and followed disease course for 2 weeks. PTPRA KO mice displayed significantly decreased arthritis severity as assessed by measurements of ankle swelling shown in FIG. 5A, joint inflammation using an intravital probe shown in FIG. 5B, bone and cartilage erosions shown in FIG. 5C and FIG. 7A, and bone mineralization using micro-computed tomography (microCT), shown in FIGS. 7B and FIGS. 7C. PTPRA KO does not cause a bone phenotype per se (33), suggesting that RPTPα promotes K/BxN serum-induced bone erosion through an effect on inflammation.

Figure 6A:
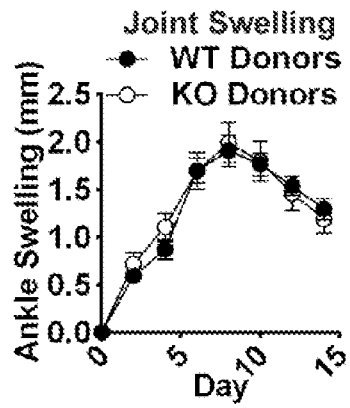
FIGS. 6A-6D. Arthritis protection in Ptpra KO mice is dependent upon radioresistant cells.
Figure 6B:
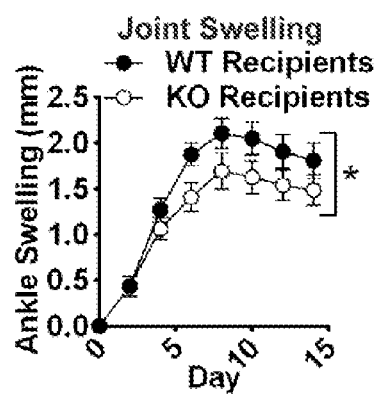
Figure 6C:
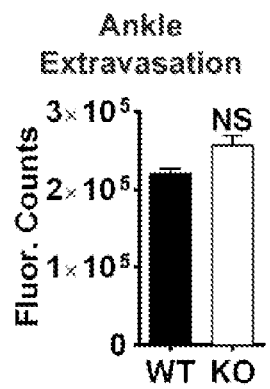
Figure 6D:
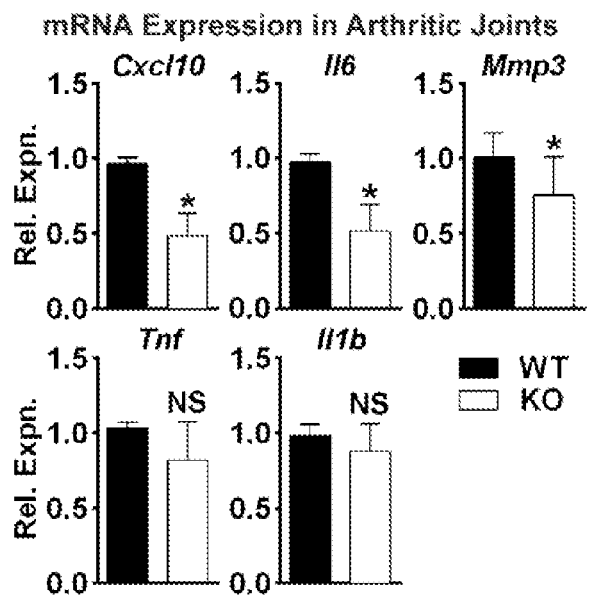

In the K/BxN serum transfer model, disease development depends primarily upon actions of innate immune cells and FLS (34-36). To determine whether disease protection in the PTPRA KO mouse is due to recruited myeloid cells or radioresistant cells, such as FLS, applicants performed reciprocal bone-marrow transplantation. WT recipient mice did not show any difference in arthritis severity after transplantation with bone-marrow from WT or PTPRA KO donor mice, as observed in FIG. 6A. However, PTPRA KO mice still showed significantly reduced severity of arthritis compared to WT mice after transplantation with bone-marrow from WT mice, shown in FIG. 6B. This data suggest that arthritis in this model is promoted by PTPRA through an effect on radioresistant cells. To rule out effects of RPTPα on radioresistant cell types that control vascular permeability, applicants examined whether PTPRA KO reduced acute K/BxN serum-induced extravasation to the ankles, and found no effect of PTPRA KO using an intravital tracer, seen in FIG. 6C. Upon examination of the expression of pathogenic mediators of disease in arthritic ankle homogenates, applicants found that PTPRA KO mice exhibited significantly reduced expression of several genes produced by FLS during arthritis, including IL6 and MMP3—two important mediators of joint destruction in RA (4, 37)—and CXCL10—a critical pathogenic factor in mouse and human RA (38,39), observed in FIG. 6D. PTPRA KO mice also exhibited slightly reduced expression of TNF and IL1b—inflammatory cytokines produced by immune cells that drive disease in the K/BxN model, also seen in FIG. 6D, likely a secondary phenomenon due to decreased inflammatory infiltrate in the PTPRA KO joint.

Example 7

Discussion

RPTPα is expressed in the primary rheumatoid synovium and in cultured FLS. Knockdown of RPTPα expression impaired RA FLS induction of pro-inflammatory and pro-invasive factors in response to TNF or IL-1β stimulation. Additionally, RPTPα knockdown reduced RA FLS invasiveness in response to PDGF, which is attributed to a combination of decreased survival, cytoskeletal reorganization and motility. Applicants assessed whether RPTPa mediates arthritis severity in the K/BxN mouse model, where FLS are critical to disease development (35). PTPRA deletion significantly reduced arthritis development, which reciprocal bone-marrow transplantation revealed was due to radioresistant cells.

The observed decreased invasiveness, motility and survival of RA FLS subjected to RPTPα knockdown is consistent with previous reports on the regulation of the SRC/FAK pathway by RPTPα in other fibroblasts (14,16). In line with these reports, applicants observed that in resting RA FLS, loss of RPTPα increased phosphorylation of SRC-Y527 and impaired FAK-Y397 phosphorylation. Applicants next investigated the RPTPα-regulated pathways downstream TNF and IL-1β, and found that RPTPα knockdown reduced JNK, p38 and AKT phosphorylation after TNF and IL-1β stimulation. Through the use of chemical inhibitors we identified the FAK-JNK pathway as responsible for the effect of RPTPα on expression of CXCL10, IL6 and MMP13 after TNF and IL-1l3 stimulation. The observed increase in IL6 expression after RA FLS treatment with the AKT inhibitor is interesting given that this compound has been shown to attenuate RA FLS migration and invasiveness (40). The effect on IL-6 suggests that the AKT pathway can have differential effects on FLS aggressive phenotypes.

RPTPα does not promote inflammation mediated by neutrophils, macrophages, or platelets, three radiosensitive cell types that contribute to pathogenicity in the K/BxN model (41-43). RPTPα did not affect K/BxN serum-induced vascular permeability, indicating no effects on endothelial cells. Mast cells are relatively radioresistant and have a controversial role in the K/BxN model (44); however PTPRA KO mice displayed increased IgE-dependent anaphylaxis, suggesting PTPRA deletion does not suppress mast cell function (45). Since disease pathogenesis in the passive K/BxN model is lymphocyte-independent (36), this model has not allowed us to examine whether there is a role for RPTPα in lymphocyte-mediated RA pathogenesis. However, peripheral T cell activation and proliferation were shown to be unaffected by PTPRA deletion (46). Since phospho-SRC-Y527 is also targeted by the highly expressed PTP CD45, which is only present in hematopoietic cells, it is likely that redundancy between RPTPα and CD45 renders RPTPα less critical in adaptive immune cell signaling.

Indeed, CD45 was reported to display much higher activity than RPTPα in T cells (47).

It was recently reported that Fak deletion reduced FLS migration and invasiveness, however global Fak KO did not affect disease severity in a TNF-induced mouse arthritis model (48). This difference can be explained by understanding the difference in arthritis phenotypes between PTPRA and Fak KO mice, which could be that deletion of Fak has opposing effects in FLS versus other arthritis-relevant cell types—such as immune cells.

This study shows that inhibition of RPTPα to be therapeutically beneficial for RA.

REFERENCES

1. Ospelt C, Neidhart M, Gay R E, Gay S. Synovial activation in rheumatoid arthritis. Frontiers in bioscience: a journal and virtual library 2004; 9:2323-34;

2. Lefevre S, Knedla A, Tennie C, Kampmann A, Wunrau C, Dinser R, et al. Synovial fibroblasts spread rheumatoid arthritis to unaffected joints. Nature medicine 2009; 15(12): 1414-20;

3. Neumann E, Lefevre S, Zimmermann B, Gay S, Muller-Ladner U. Rheumatoid arthritis progression mediated by activated synovial fibroblasts. Trends Mol Med 2010; 16(10):458-68;

4. Bottini N, Firestein G S. Duality of fibroblast-like synoviocytes in RA: passive responders and imprinted aggressors. Nat Rev Rheumato12013; 9(1):24-33;

5. Noss E H, Brenner M B. The role and therapeutic implications of fibroblast-like synoviocytes in inflammation and cartilage erosion in rheumatoid arthritis Immunological reviews 2008; 223 :252-70;

6. Niedermeier M, Pap T, Korb A. Therapeutic opportunities in fibroblasts in inflammatory arthritis. Best Pract Res Clin Rheumatol 2010; 24(4):527-40;

7. Mitra S K, Hanson D A, Schlaepfer D D. Focal adhesion kinase: in command and control of cell motility. Nature reviews. Molecular cell biology 2005; 6(1):56-68;

8. Hanks S K, Ryzhova L, Shin N Y, Brabek J. Focal adhesion kinase signaling activities and their implications in the control of cell survival and motility. Frontiers in bioscience : a journal and virtual library 2003; 8:d982-96;

9. Shahrara S, Castro-Rueda H P, Haines G K, Koch A E. Differential expression of the FAK family kinases in rheumatoid arthritis and osteoarthritis synovial tissues. Arthritis research & therapy 2007; 9(5):R112;

10. Nakano K, Whitaker J W, Boyle D L, Wang W, Firestein G S. DNA methylome signature in rheumatoid arthritis. Ann Rheum Dis 2013; 72(1):110-7;

11. Stanford S M, Maestre M F, Campbell A M, Bartok B, Kiosses W B, Boyle D L, et al. Protein tyrosine phosphatase expression profile of rheumatoid arthritis fibroblast-like synoviocytes: a novel role of SH2 domain-containing phosphatase 2 as a modulator of invasion and survival. Arthritis Rheum 2013; 65(5):1171-80;

12. Zeng L, Si X, Yu W P, Le H T, Ng K P, Teng R M, et al. PTP alpha regulates integrin-stimulated FAK autophosphorylation and cytoskeletal rearrangement in cell spreading and migration. J Cell Biol 2003; 160(1):137-46;

13. Cheng S Y, Sun G, Schlaepfer D D, Fallen C J. Grb2 promotes integrin-induced focal adhesion kinase (FAK) autophosphorylation and directs the phosphorylation of protein tyrosine phosphatase alpha by the Src-FAK kinase complex. Mol Cell Biol 2014; 34(3):348-61;

14. Su J, Muranjan M, Sap J. Receptor protein tyrosine phosphatase alpha activates Src-family kinases and controls integrin-mediated responses in fibroblasts. Curr Biol 1999; 9(10):505-11;

15. Sap J, D'Eustachio P, Givol D, Schlessinger J. Cloning and expression of a widely expressed receptor tyrosine phosphatase. Proc Natl Acad Sci USA 1990; 87(16):6112-6;

16. Pallen C J. Protein tyrosine phosphatase alpha (PTPalpha): a Src family kinase activator and mediator of multiple biological effects. Curr Top Med Chem 2003; 3(7):821-35;

17. Zheng X M, Wang Y, Pallen C J. Cell transformation and activation of pp60c-src by overexpression of a protein tyrosine phosphatase. Nature 1992; 359(6393):336-9;

18. den Hertog J, Pals C E, Peppelenbosch M P, Tertoolen L G, de Laat S W, Kruijer W. Receptor protein tyrosine phosphatase alpha activates pp60c-src and is involved in neuronal differentiation. EMBO J 1993; 12(10):3789-98;

19. Ponniah S, Wang D Z, Lim K L, Pallen C J. Targeted disruption of the tyrosine phosphatase PTPalpha leads to constitutive downregulation of the kinases Src and Fyn. Curr Biol 1999; 9(10):535-8;

20. Aschner Y, Khalifah A P, Briones N, Yamashita C, Dolgonos L, Young S K, et al. Protein tyrosine phosphatase alpha mediates profibrotic signaling in lung fibroblasts through TGF-beta responsiveness. Am J Pathol 2014; 184 (5):1489-502;

21. Alvaro-Gracia J M, Zvaifler N J, Brown C B, Kaushansky K, Firestein G S. Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-alpha. Journal of immunology 1991; 146(10):3365-71;

22. Arnett F C, Edworthy S M, Bloch D A, McShane D J, Fries J F, Cooper N S, et al. The American Rheumatism Association 1987 revised criteria for the classification of rheumatoid arthritis. Arthritis and rheumatism 1988; 31(3): 315-24;

23. Radonic A, Thulke S, Mackay I M, Landt O, Siegert W, Nitsche A. Guideline to reference gene selection for quantitative real-time PCR. Biochemical and biophysical research communications 2004; 313(4):856-62;

24. Laragione T, Brenner M, Mello A, Symons M, Gulko P S. The arthritis severity locus Cia5d is a novel genetic regulator of the invasive properties of synovial fibroblasts. Arthritis and rheumatism 2008; 58(8):2296-306;

25. Tolboom T C, van der Helm-Van Mil A H, Nelissen R G, Breedveld F C, Toes R E, Huizinga TW. Invasiveness of fibroblast-like synoviocytes is an individual patient characteristic associated with the rate of joint destruction in patients with rheumatoid arthritis. Arthritis and rheumatism 2005; 52(7):1999-2002;

26. Bodrikov V, Leshchyns'ka I, Sytnyk V, Overvoorde J, den Hertog J, Schachner M. RPTPalpha is essential for NCAM-mediated p59fyn activation and neurite elongation. J Cell Biol 2005; 168(1):127-39;

27. Monach P A, Mathis D, Benoist C. The K/BxN arthritis model. Curr Protoc Immunol 2008; Chapter 15:Unit 15 22.

28. Guma M, Ronacher L, Liu-Bryan R, Takai S, Karin M, Corr M. Caspase 1-independent activation of interleukin-1beta in neutrophil-predominant inflammation. Arthritis Rheum 2009; 60(12):3642-50;

29. Wang Q, Rajshankar D, Branch D R, Siminovitch K A, Herrera Abreu M T, Downey G P, et al. Protein-tyrosine phosphatase-alpha and Src functionally link focal adhesions to the endoplasmic reticulum to mediate interleukin-1-induced Ca2+ signaling. J Biol Chem 2009; 284(31):20763-72;

30. Wang Q, Rajshankar D, Laschinger C, Talior-Volodarsky I, Wang Y, Downey G P, et al. Importance of protein-tyrosine phosphatase-alpha catalytic domains for interactions with SHP-2 and interleukin-1-induced matrix metalloproteinase-3 expression. J Biol Chem 2010; 285(29): 22308-17;

31. Rajshankar D, Sima C, Wang Q, Goldberg S R, Kazembe M, Wang Y, et al. Role of PTPalpha in the destruction of periodontal connective tissues. PLoS One 2013; 8(8):e70659;

32. Stanford S M, Aleman Muench G R, Bartok B, Sacchetti C, Kiosses W B, Sharma J, et al. TGFbeta responsive tyrosine phosphatase promotes rheumatoid synovial fibroblast invasiveness. Ann Rheum Dis 2014;

33. Finkelshtein E, Lotinun S, Levy-Apter E, Arman E, den Hertog J, Baron R, et al. Protein tyrosine phosphatases epsilon and alpha perform nonredundant roles in osteoclasts. Mol Biol Cell 2014; 25(11):1808-18.

34. Ji H, Ohmura K, Mahmood U, Lee D M, Hofhuis F M, Boackle S A, et al. Arthritis critically dependent on innate immune system players. Immunity 2002; 16(2):157-68;

35. Lee DM, Kiener H P, Agarwal S K, Noss E H, Watts G F, Chisaka O, et al. Cadherin-11 in synovial lining formation and pathology in arthritis. Science 2007; 315 (5814):1006-10;

36. Wang Y, Shaked I, Stanford S M, Zhou W, Curtsinger J M, Mikulski Z, et al. The autoimmunity-associated gene PTPN22 potentiates toll-like receptor-driven, type 1 interferon-dependent immunity. Immunity 2013; 39(1):111-22;

37. Baumann H, Kushner I. Production of interleukin-6 by synovial fibroblasts in rheumatoid arthritis. Am J Pathol 1998; 152(3):641-4;

38. Hanaoka R, Kasama T, Muramatsu M, Yajima N, Shiozawa F, Miwa Y, et al. A novel mechanism for the regulation of IFN-gamma inducible protein-10 expression in rheumatoid arthritis. Arthritis Res Ther 2003; 5(2):R74-81;

39. Lee E Y, Lee Z H, Song Y W. The interaction between CXCL10 and cytokines in chronic inflammatory arthritis. Autoimmun Rev 2013; 12(5):554-7;

40. Fan W, Zhou Z Y, Huang X F, Bao C D, Du F. Deoxycytidine kinase promotes the migration and invasion of fibroblast-like synoviocytes from rheumatoid arthritis patients. Int J Clin Exp Pathol 2013; 6(12):2733-44;

41. Wipke B T, Allen P M. Essential role of neutrophils in the initiation and progression of a murine model of rheumatoid arthritis. J Immunol 2001; 167(3):1601-8;

42. Boilard E, Nigrovic P A, Larabee K, Watts G F, Coblyn J S, Weinblatt M E, et al. Platelets amplify inflammation in arthritis via collagen-dependent microparticle production. Science 2010; 327(5965):580-3;

43. Guma M, Hammaker D, Topolewski K, Corr M, Boyle D L, Karin M, et al. Antiinflammatory functions of p38 in mouse models of rheumatoid arthritis: advantages of targeting upstream kinases MKK-3 or MKKk-6. Arthritis and rheumatism 2012; 64(9):2887-95;

44. Nigrovic P A, Malbec O, Lu B, Markiewski MM, Kepley C, Gerard N, et al. C5a receptor enables participation of mast cells in immune complex arthritis independently of Fcgamma receptor modulation. Arthritis Rheum 2010; 62(11):3322-33.

45. Samayawardhena L A, Pallen C J. PTPalpha activates Lyn and Fyn and suppresses Hck to negatively regulate FcepsilonR1-dependent mast cell activation and allergic responses. J Immunol 2010; 185(10):5993-6002;

46. Maksumova L, Le H T, Muratkhodjaev F, Davidson D, Veillette A, Pallen C J. Protein tyrosine phosphatase alpha regulates Fyn activity and Cbp/PAG phosphorylation in thymocyte lipid rafts. J Immunol 2005; 175(12):7947-56;

47. Ng D H, Jabali M D, Maiti A, Borodchak P, Harder K W, Brocker T, et al. CD45 and RPTPalpha display different protein tyrosine phosphatase activities in T lymphocytes. Biochem J 1997; 327 (Pt 3):867-76;

48. Shelef M A, Bennin D A, Yasmin N, Warner T F, Ludwig T, Beggs H E, et al. Focal adhesion kinase is required for synovial fibroblast invasion, but not murine inflammatory arthritis. Arthritis Res Ther 2014; 16(5):464;

49. Gil-Henn H, Elson A. Tyrosine phosphatase-epsilon activates Src and supports the transformed phenotype of Neu-induced mammary tumor cells. J Biol Chem 2003; 278(18):15579-86;

50. Zheng X, Resnick R J, Shalloway D. Apoptosis of estrogen-receptor negative breast cancer and colon cancer cell lines by PTP alpha and src RNAi. Int J Cancer 2008; 122(9):1999-2007.

EMBODIMENTS

Embodiments include embodiments P1 to P15 following.

Embodiment P1. A method of treating a subject who has or is at risk of developing an autoimmune disease, the method comprising administering to the subject a therapeutically effective amount of an autoimmune therapeutic agent, wherein the autoimmune therapeutic agent is an agonist or an antagonist of PTPRA.

Embodiment P2. The method of embodiment P1, wherein the autoimmune disease is an inflammatory autoimmune disease and the autoimmune therapeutic agent is an IAD therapeutic agent, the IAD therapeutic agent selected from an anti-PTPRA antibody, an anti-PTPRA inhibitory nucleic acid and a PTPRA ligand mimetic, wherein the IAD therapeutic agent targets PTPRA, or a fragment, agonist or antagonist thereof.

Embodiment P3. The method embodiment P1 or embodiment P2 wherein the autoimmune therapeutic agent is an antagonist of PTPRA.

Embodiment P4. The method of embodiment P2, wherein the inflammatory autoimmune disease is mediated by cells expressing PTPRA.

Embodiment P5. The method of embodiment P4, wherein the cells are fibroblast-like synoviocytes.

Embodiment P6. The method embodiment P2 or embodiment P3, wherein the inflammatory autoimmune disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, or allergic asthma.

Embodiment P7. The method of one of embodiments P2, P3, or P6, wherein the inflammatory autoimmune disease is rheumatoid arthritis.

Embodiment P8. The method of any one of embodiments P1 to P7 wherein the method comprises decreasing, reducing, inhibiting, suppressing, limiting or controlling TNF and PDGF activity.

Embodiment P9. A pharmaceutical composition comprising an autoimmune therapeutic agent and a pharmaceutically acceptable excipient, wherein the autoimmune therapeutic agent is an agonist or antagonist of PTRPA.

Embodiment P10. The pharmaceutical composition of embodiment P9 wherein the autoimmune therapeutic agent is an antagonist of PTPRA.

Embodiment P11. The pharmaceutical composition of embodiment P9 or embodiment P10, wherein the pharmaceutical composition comprises an IAD therapeutic agent and a pharmaceutically acceptable excipient, wherein the IAD therapeutic agent is an IAD therapeutic agent selected from an anti-PTPRA antibody, an anti-PTPRA inhibitory nucleic acid or PTPRA ligand mimetic.

Embodiment P12. The pharmaceutical composition of embodiment P11, wherein the IAD therapeutic agent is an anti-PTPRA antibody.

Embodiment P13. The pharmaceutical composition of embodiment P11, wherein the IAD therapeutic agent is an anti-PTPRA inhibitory nucleic acid.

Embodiment P14. The pharmaceutical composition of embodiment P13, wherein the anti-PTPRA inhibitory nucleic acid is an anti-PTPRA antisense nucleic acid.

Embodiment P15. The pharmaceutical composition of embodiment P11, wherein the PTPRA ligand mimetic is a peptide or a small chemical molecule.

Further embodiments include the following:

Embodiment 1. A method of treating an autoimmune disease in a subject in need thereof, the method comprising administering to the subject an effective amount of a PTPRA antagonist.

Embodiment 2. The method of embodiment 1, wherein said autoimmune disease is a fibroblast mediated disease, arthritis, osteoarthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, scleroderma, systemic sclerosis, or allergic asthma.

Embodiment 3. A method of decreasing inflammation in a synovium of a subject in need thereof, the method comprising administering to the subject an effective amount of a PTPRA antagonist.

Embodiment 4. The method of any one of embodiments 1, 2 or 3, wherein said subject comprises fibroblast-like synoviocytes that express high levels of PTPRA relative to a standard control.

Embodiment 5. The method of any one of embodiments 3 or 4, wherein said subject has rheumatoid arthritis.

Embodiment 6. A method of decreasing expression of PTPRA in a fibroblast-like synoviocyte, the method comprising contacting said fibroblast-like synoviocyte with an effective amount of a PTPRA antagonist.

Embodiment 7. A method of decreasing TNF activity, IL-1 activity or PDGF activity in a fibroblast-like synoviocyte, the method contacting said fibroblast-like synoviocyte with an effective amount of a PTPRA antagonist.

Embodiment 8. The method of embodiment 7, consisting of decreasing TNF activity or IL-1 activity.

Embodiment 9. The method of any one of embodiments 7 or 8, wherein said decreasing comprises decreasing expression of TNF or IL-1.

Embodiment 10. A method of decreasing invasiveness or migration of a fibroblast-like synoviocyte, the method comprising contacting said fibroblast-like synoviocyte with an effective amount of a PTPRA antagonist.

Embodiment 11. The method of any one embodiments 6 to 10, wherein said fibroblast-like synoviocyte is a rheumatoid arthritis fibroblast-like synoviocyte.

Embodiment 12. The method of any one embodiments 6 to 11, wherein said fibroblast-like synoviocyte expresses high levels of PTPRA relative to a standard control.

Embodiment 13. The method of one of embodiments 1 to 12, wherein said PTPRA antagonist is an anti-PTPRA antibody, an anti-PTPRA inhibitory nucleic acid or a PTPRA ligand mimetic.

Embodiment 14. The method of embodiment 13, wherein said anti-PTPRA antibody is an anti-PTPRA extracellular antibody.

Embodiment 15. The method of embodiment 13, wherein said anti-PTPRA antibody is an anti-PTPRA dimer inhibiting antibody or a anti-PTPRA dimerizing antibody.

Embodiment 16. The method of embodiment 13, wherein said anti-PTPRA inhibitory nucleic acid has at least 90% sequence identity to an at least 10 nucleotide contiguous sequence of SEQ ID NO: 1, SEQ ID NO:2, SEQ ID NO:3 or a complementary sequence thereof Embodiment 17. The method of embodiment 13, wherein said anti-PTPRA ligand mimetic is a peptide or a small chemical molecule.

Embodiment 18. A pharmaceutical composition comprising a PTPRA antagonist and a pharmaceutically acceptable excipient.

Embodiment 19. The pharmaceutical composition of embodiment 18, wherein said PTPRA antagonist is an anti-PTPRA antibody, an anti-PTPRA inhibitory nucleic acid or a PTPRA ligand mimetic.

Embodiment 20. The pharmaceutical composition of embodiment 18, wherein said anti-PTPRA antibody is an anti-PTPRA extracellular antibody.

Embodiment 21. The pharmaceutical composition of embodiment 18, wherein said anti-PTPRA antibody is an anti-PTPRA dimer inhibiting antibody or an anti-PTPRA dimerizing antibody.

Embodiment 22. The pharmaceutical composition of embodiment 18, wherein said anti-PTPRA inhibitory nucleic acid has at least 90% sequence identity to at least 10 nucleotide contiguous sequence of SEQ ID NO: 1, SEQ ID NO: 2, SEQ ID NO: 3 or a complementary sequence thereof.

Embodiment 23. The pharmaceutical composition of embodiment 18, wherein said anti-PTPRA ligand mimetic is a peptide or a small chemical molecule.

Further embodiments include embodiments W1-W81 the following:

Embodiment W1. A method of treating an autoimmune disease in a subject in need thereof, the method comprising administering to said subject an effective amount of a protein tyrosine phosphatase receptor type A (PTPRA) antagonist, thereby treating an autoimmune disease in said subject.

Embodiment W2. The method of embodiment W1, wherein said PTPRA antagonist is an anti-PTPRA antibody, an anti-PTPRA inhibitory nucleic acid, a peptide, a protein or a small molecule.

Embodiment W3. The method of embodiment W2, wherein said anti-PTPRA antibody binds an extracellular portion of PTPRA.

Embodiment W4. The method of embodiment W1 or W2, wherein said PTPRA antagonist is an anti-PTPRA dimer inhibiting antibody or an anti-PTPRA dimerizing antibody.

Embodiment W5. The method of embodiment W2, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof Embodiment W6. The method of embodiment W2, wherein said anti-PTPRA inhibitory nucleic acid has at least 90% sequence identity to at least 10 contiguous nucleotides of SEQ ID NO: 1, or a complementary sequence thereof.

Embodiment W7. The method of embodiment W2, wherein said anti-PTPRA inhibitory nucleic acid has at least 90% sequence identity to at least 10 contiguous nucleotides of SEQ ID NO: 2 or a complementary sequence thereof.

Embodiment W8. The method of embodiment W2, wherein said anti-PTPRA inhibitory nucleic acid has at least 90% sequence identity to at least 10 contiguous nucleotides of SEQ ID NO: 3 or a complementary sequence thereof.

Embodiment W9. The method of one of embodiments W2 or W5-W8, wherein said anti-PTPRA inhibitory nucleic acid is a morpholino nucleic acid.

Embodiment W10. The method of embodiment W9, wherein said morpholino nucleic acid is a single stranded antisense nucleic acid.

Embodiment W11. The pharmaceutical composition of embodiment W10, wherein said morpholino nucleic acid is a phosphoramidate morpholino nucleic acid.

Embodiment W12. The method of embodiment W9, wherein said morpholino nucleic acid is conjugated to a cell permeable moiety.

Embodiment W13. The method of one of embodiments W1 or W2, wherein said PTPRA antagonist is a peptide or a small molecule.

Embodiment W14. The method of one of embodiments W1-W13, wherein said autoimmune disease is arthritis or a fibroblast mediated disease.

Embodiment W15. The method of embodiment W14, wherein said arthritis is rheumatoid arthritis, psoriatic arthritis, juvenile idiopathic arthritis, or osteoarthritis.

Embodiment W16. The method of one of embodiments W1-W13, wherein said autoimmune disease is multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, scleroderma, systemic sclerosis, or allergic asthma.

Embodiment W17. The method of one of embodiments W1-W16, wherein said subject expresses elevated levels of PTPRA relative to a standard control.

Embodiment W18. The method of one of embodiments W1-W17, wherein said subject comprises fibroblast-like synoviocytes expressing elevated levels of PTPRA relative to a standard control.

Embodiment W19. The method of one of embodiments W1-W18, further comprising administering to said subject an effective amount of a further therapeutic agent.

Embodiment W20. A method of identifying a PTPRA antagonist, the method comprising: (i) contacting a test agent with a sarcoma tyrosine kinase (SRC)-expressing cell in vitro, thereby forming a contacted cell; and (ii) determining in said contacted cell a level of SRC Tyr527 phosphorylation, wherein an increased level of SRC Tyr527 phosphorylation indicates said test agent is a PTPRA antagonist, thereby identifying a PTPRA antagonist.

Embodiment W21. A method of identifying a PTPRA antagonist, the method comprising: (i) contacting a test agent with a focal adhesion kinase (FAK)-expressing cell in vitro, thereby forming a contacted cell; and (ii) determining in said contacted cell a level of FAK Tyr397 phosphorylation, wherein a decreased level of FAK Tyr397 phosphorylation indicates said test agent is a PTPRA antagonist, thereby identifying a PTPRA antagonist.

Embodiment W22. The method of embodiment W20 or W21, wherein said cell is a fibroblast-like synoviocyte.

Embodiment W23. The method of one of embodiments W20-W23, wherein said cell is derived from a subject having or being at risk for developing an autoimmune disease.

Embodiment W24. A method of treating an autoimmune disease in a subject in need thereof, said method comprising: (i) determining whether a subject expresses an elevated level of a PTPRA protein relative to a standard control; and (ii) when an elevated expression level of said PTPRA protein is found relative to said standard control, administering to said subject a PTPRA antagonist, thereby treating an autoimmune disease in said subject.

Embodiment W25. The method of embodiment W24, wherein said PTPRA antagonist is an anti-PTPRA antibody, an anti-PTPRA inhibitory nucleic acid, a peptide, a protein or a small molecule.

Embodiment W26. The method of embodiment W25, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof Embodiment W27. The method of embodiment W25, wherein said anti-PTPRA inhibitory nucleic acid is a morpholino nucleic acid.

Embodiment W28. The method of embodiment W27, wherein said morpholino nucleic acid is a single stranded antisense nucleic acid.

Embodiment W29. The method of embodiment W27, wherein said morpholino nucleic acid is a phosphoramidate morpholino nucleic acid.

Embodiment W30. The method of embodiment W27, wherein said morpholino nucleic acid is conjugated to a cell permeable moiety.

Embodiment W31. The method of embodiment W25, wherein said PTPRA antagonist is a peptide or a small molecule.

Embodiment W32. The method of one of embodiments W24-W31, wherein said autoimmune disease is arthritis or a fibroblast mediated disease.

Embodiment 33. The method of one of embodiments W24-W32, wherein said arthritis is rheumatoid arthritis, psoriatic arthritis, juvenile idiopathic arthritis, or osteoarthritis.

Embodiment W34. The method of one of embodiments W24-W31, wherein said autoimmune disease is multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, scleroderma, systemic sclerosis, or allergic asthma.

Embodiment W35. The method of one of embodiments W24-W34, further comprising administering to said subject an effective amount of a further therapeutic agent.

Embodiment W36. A method of determining an expression level of a PTPRA protein in a subject that has or is at risk for developing an autoimmune disease, said method comprising:
(i) obtaining a biological sample from said subject; and
(ii) determining an expression level of a PTPRA protein in said biological sample.

Embodiment W37. The method of embodiment W36, wherein said determining comprises: (a) contacting a PTPRA protein with a protein binding agent in said biological sample, thereby forming a PTPRA protein-binding agent complex; and (b) detecting said PTPRA protein-binding agent complex.

Embodiment W38. The method of embodiment W37, wherein said protein binding agent comprises a detectable moiety.

Embodiment W39. The method of embodiment W36, further comprising selecting a subject that has or is at risk for developing an autoimmune disease.

Embodiment W40. The method of embodiment W36, further comprising administering to said subject an effective amount of a PTPRA antagonist.

Embodiment W41. The method of embodiment W40, wherein said PTPRA antagonist is an anti-PTPRA antibody, an anti-PTPRA inhibitory nucleic acid, a peptide, a protein or a small molecule.

Embodiment W42. The method of embodiment W41, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof Embodiment W43. The method of embodiment W41, wherein said anti-PTPRA inhibitory nucleic acid is a morpholino nucleic acid.

Embodiment W44. The method of embodiment W43, wherein said morpholino nucleic acid is a single stranded antisense nucleic acid.

Embodiment W45. The method of embodiment W43, wherein said morpholino nucleic acid is a phosphoramidate morpholino nucleic acid.

Embodiment W46. The method of embodiment W43, wherein said morpholino nucleic acid is conjugated to a cell permeable moiety.

Embodiment W47. The method of embodiment W41, wherein said PTPRA antagonist is a peptide or a small molecule.

Embodiment W48. The method of one of embodiments W36-W47, wherein said expression level of said PTPRA protein is elevated relative to a standard control.

Embodiment W49. The method of one of embodiments W36-W48, wherein said PTPRA protein is expressed in a fibroblast-like synoviocyte.

Embodiment W50. The method of one of embodiments W36-W49, further comprising administering to said subject an effective amount of a further therapeutic agent.

Embodiment W51. A complex in vitro comprising a protein binding agent bound to a PTPRA protein or fragment thereof, wherein said PTPRA protein is extracted from a human subject having or being at risk of developing an autoimmune disease.

Embodiment W52. The complex of embodiment W51, wherein said subject has an autoimmune disease.

Embodiment W53. The complex of embodiment W51 or W52, wherein said PTPRA protein is extracted from a fibroblast-like synoviocyte.

Embodiment W54. A method of inhibiting PTPRA protein activity in a cell, the method comprising contacting a cell with an effective amount of a PTPRA antagonist thereby inhibiting PTPRA protein activity in said cell.

Embodiment W55. The method of embodiment W54, wherein said cell is a fibroblast-like synoviocyte, Embodiment W56. The method of embodiment W54, wherein said PTPRA antagonist is an anti-PTPRA antibody, an anti-PTPRA inhibitory nucleic acid, peptide, or a small molecule.

Embodiment W57. The method of embodiment W56, wherein said anti-PTPRA antibody binds an extracellular portion of PTPRA.

Embodiment W58. The method of embodiment W54, wherein said PTPRA antagonist is an anti-PTPRA dimer inhibiting antibody or an anti-PTPRA dimerizing antibody.

Embodiment W59. The method of embodiment W56, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof Embodiment W60. The method of embodiment W56, wherein said anti-PTPRA inhibitory nucleic acid has at least 90% sequence identity to at least 10 contiguous nucleotides of SEQ ID NO: 1, or a complementary sequence thereof.

Embodiment W61. The method of embodiment W56, wherein said anti-PTPRA inhibitory nucleic acid has at least 90% sequence identity to at least 10 contiguous nucleotides of SEQ ID NO: 2 or a complementary sequence thereof.

Embodiment W62. The method of embodiment W56, wherein said anti-PTPRA inhibitory nucleic acid has at least 90% sequence identity to at least 10 contiguous nucleotides of SEQ ID NO: 3 or a complementary sequence thereof.

Embodiment W63. The method of one of embodiments W56 or W59-W62, wherein said anti-PTPRA inhibitory nucleic acid is a morpholino nucleic acid.

Embodiment W64. The method of embodiment W63, wherein said morpholino nucleic acid is a single stranded antisense nucleic acid.

Embodiment W65. The method of embodiment W63, wherein said morpholino nucleic acid is a phosphoramidate morpholino nucleic acid.

Embodiment W66. The method of embodiment W63, wherein said morpholino nucleic acid is conjugated to a cell permeable moiety.

Embodiment W67. The method of embodiment W54, wherein said PTPRA antagonist is a peptide or a small molecule.

Embodiment W68. A pharmaceutical composition comprising a PTPRA antagonist and a pharmaceutically acceptable recipient.

Embodiment W69. The pharmaceutical composition of embodiment W68, wherein said PTPRA antagonist is an anti-PTPRA antibody, an anti-PTPRA inhibitory nucleic acid, a peptide, a protein or a small molecule.

Embodiment W70. The pharmaceutical composition of embodiment W69, wherein said anti-PTPRA antibody binds an extracellular portion of PTPRA.

Embodiment W71. The pharmaceutical composition of embodiment W68, wherein said PTPRA antagonist is an anti-PTPRA dimer inhibiting antibody or an anti-PTPRA dimerizing antibody.

Embodiment W72. The pharmaceutical composition of embodiment W69, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof.

Embodiment W73. The pharmaceutical composition of embodiment W72, wherein said anti-PTPRA inhibitory nucleic acid is a morpholino nucleic acid.

Embodiment W74. The pharmaceutical composition of embodiment W73, wherein said morpholino nucleic acid is a single stranded antisense nucleic acid.

Embodiment W75. The pharmaceutical composition of embodiment W74, wherein said morpholino nucleic acid is a phosphoramidate morpholino nucleic acid.

Embodiment W76. The pharmaceutical composition of embodiment W73, wherein said morpholino nucleic acid is conjugated to a cell permeable moiety.

Embodiment W77. The pharmaceutical composition of embodiment W69, wherein said PTPRA antagonist is a peptide or a small molecule.

Embodiment W78. A method of decreasing inflammation in a synovium of a subject in need thereof, the method comprising administering to the subject an effective amount of a PTPRA antagonist, wherein said PTPRA antagonist is an anti-PTPRA antibody, an anti-PTPRA inhibitory nucleic acid, peptide, or a small molecule.

Embodiment W79. A method of inhibiting expression of a growth factor in a fibroblast-like synoviocyte, the method comprising contacting said fibroblast-like synoviocyte with an effective amount of a PTPRA antagonist, thereby inhibiting expression of a growth factor in a fibroblast-like synoviocyte, Embodiment W80. A method of inhibiting expression of inflammatory cytokines in a fibroblast-like synoviocyte, the method comprising contacting said fibroblast-like synoviocyte with an effective amount of a PTPRA antagonist, thereby inhibiting expression of inflammatory cytokines in a fibroblast-like synoviocyte.

Embodiment W81. The method of embodiment W80, wherein said inflammatory cytokines are tumor necrosis factor-alpha (TNF), interleukin-6 (IL-6) or interleukin-1 (IL-1).

Embodiment W82. A method of inhibiting expression of a matrix metalloproteinase in a fibroblast-like synoviocyte, the method comprising contacting said fibroblast-like synoviocyte with an effective amount of a PTPRA antagonist, thereby inhibiting expression of a matrix metalloproteinase in said fibroblast-like synoviocyte.

Embodiment W83. The method of embodiment W9, wherein said morpholino nucleic acid has the sequence of SEQ ID NO:4 or SEQ ID NO:5.

Embodiment W84. The method of embodiment W27, wherein said morpholino nucleic acid has the sequence of SEQ ID NO:4 or SEQ ID NO:5.

Embodiment W85. The method of embodiment W43, wherein said morpholino nucleic acid has the sequence of SEQ ID NO:4 or SEQ ID NO:5.

Embodiment W86. The method of embodiment W63, wherein said morpholino nucleic acid has the sequence of SEQ ID NO:4 or SEQ ID NO:5.

Embodiment W87. The pharmaceutical composition of embodiment W73, wherein said morpholino nucleic acid has the sequence of SEQ ID NO:4 or SEQ ID NO:5.

Sequences

Homo sapiens protein tyrosine phosphatase, receptor type, A (PTPRA), transcript variant 1 (NCBI Accession No. NM_002836.3):

```
                                              (SEQ ID NO: 1)
CACGCTCAGGGGAGCAGGTACCCCTTCTCCTAAAGATGAAGAGGAGCA

AACTGGCACTAAGCAAGGCCATCGAGAGCGGGGACACTGACCTGGTGT

TCACGGTGTTGCTGCACCTGAAGAACGAGCTGAACCGAGGAGATTTTT

TCATGACCCTTCGGAATCAGCCCATGGCCCTCAGTTTGTACCGACAGT

TCTGTAAGCATCAGGAGCTAGAGACGCTGAAGGACCTTTACAATCAGG

ATGACAATCACCAGGAATTGGGCAGCTTCCACATCCGAGCCAGCTATG

CTGCAGAAGAGCGTATTGAGGGGCGAGTAGCAGCTCTGCAGACAGCCG

CCGATGCCTTCTACAAGGCCAAGAATGAGTTTGCAGCCAAGGCTACAG

AGGATCAAATGCGGCTCCTACGGCTGCAGCGGCGCCTAGAAGACGAGC

TGGGGGGCCAGTTCCTAGACCTGTCTCTACATGACACAGTTACCACCC

TCATTCTTGGCGGTCACAACAAGCGTGCAGAGCAGCTGGCACGTGACT

TCCGCATCCCTGACAAGAGGTGACACAACTAAAAAAAAACAAAGGTAT

TTATGGAATTCCACTGAGTGGTAATGGATGATGCAGTTCAAATAACTA

AGGACACATGTTCAAAGAGCATAATTAACTTTTTAAAAGAAGCTAATA

AGCATGGATTCCTGGTTCATTCTTGTTCTGCTCGGCAGTGGTCTGATA

TGTGTCAGTGCCAACAATGCTACCACAGTTGCACCTTCTGTAGGAATT

ACAAGATTAATTAACTCATCAACGGCAGAACCAGTTAAAGAAGAGGCC

AAAACTTCAAATCCAACTTCTTCACTAACTTCTCTTTCTGTGGCACCA

ACATTCAGCCCAAATATAACTCTGGGACCCACCTATTTAACCACTGTC

AATTCTTCAGACTCTGACAATGGGACCACAAGAACAGCAAGCACCAAT

TCTATAGGCATTACAATTTCACCAAATGGAACGTGGCTTCCAGATAAC

CAGTTCACGGATGCCAGAACAGAACCCTGGGAGGGGAATTCCAGCACC

GCAGCAACCACTCCAGAAACTTTCCCTCCTTCAGGTAATTCTGACTCG

AAGGACAGAAGAGATGAGACACCAATTATTGCGGTGATGGTGGCCCTG

TCCTCTCTGCTAGTGATCGTGTTTATTATCATAGTTTTGTACATGTTA

AGGTTTAAGAAATACAAGCAAGCTGGGAGCCATTCCAATTCTTTCCGC

TTATCCAACGGCCGCACTGAGGATGTGGAGCCCCAGAGTGTGCCACTT

CTGGCCAGATCCCCAAGCACCAACAGGAAATACCCACCCCTGCCCGTG

GACAAGCTGGAAGAGGAAATTAACCGGAGAATGGCAGACGACAATAAG

CTCTTCAGGGAGGAATTCAACGCTCTCCCTGCATGTCCTATCCAGGCC

ACCTGTGAGGCTGCTTCCAAGGAGGAAAACAAGGAAAAAAATCGATAT

GTAAACATCTTGCCTTATGACCACTCTAGAGTCCACCTGACACCGGTT

GAAGGGGTTCCAGATTCTGATTACATCAATGCTTCATTCATCAACGGC

TACCAAGAAAAGAACAAATTCATTGCTGCACAAGGACCAAAAGAAGAA

ACGGTGAATGATTTCTGGCGGATGATCTGGGAACAAAACACAGCCACC

ATCGTCATGGTTACCAACCTGAAGGAGAGAAAGGAGTGCAAGTGCGCC

CAGTACTGGCCAGACCAAGGCTGCTGGACCTATGGGAATATTCGGGTG

TCTGTAGAGGATGTGACTGTCCTGGTGGACTACACAGTACGGAAGTTC

TGCATCCAGCAGGTGGGCGACATGACCAACAGAAAGCCACAGCGCCTC

ATCACTCAGTTCCACTTTACCAGCTGGCCAGACTTTGGGGTGCCTTTT

ACCCCGATCGGCATGCTCAAGTTCCTCAAGAAGGTGAAGGCCTGTAAC

CCTCAGTATGCAGGGGCCATCGTGGTCCACTGCAGTGCAGGTGTAGGG

CGTACAGGTACCTTTGTCGTCATTGATGCCATGCTGGACATGATGCAT

ACAGAACGGAAGGTGGACGTGTATGGCTTTGTGAGCCGGATCCGGGCA

CAGCGCTGCCAGATGGTGCAAACCGATATGCAGTATGTCTTCATATAC

CAAGCCTTCTGGAGCATTATCTCTATGGAGATACAGAACTGGAAGTG

ACCTCTCTAGAAACCCACCTGCAGAAAATTTACAACAAAATCCCAGGG

ACCAGCAACAATGGATTAGAGGAGGAGTTTAAGAAGTTAACATCAATC

AAAATCCAGAATGACAAGATGCGGACTGGAAACCTTCCAGCCAACATG

AAGAAGAACCGTGTTTTACAGATCATTCCATATGAATTCAACAGAGTG

ATCATTCCAGTTAAGCGGGGCGAAGAGAATACAGACTATGTGAACGCA

TCCTTTATTGATGGCTACCGGCAGAAGGACTCCTATATCGCCAGCCAG

GGCCCTCTTCTCCACACAATTGAGGACTTCTGGCGAATGATCTGGGAG

TGGAAATCCTGCTCTATCGTGATGCTAACAGAACTGGAGGAGAGAGGC

CAGGAGAAGTGTGCCCAGTACTGGCCATCTGATGGACTGGTGTCCTAT

GGAGATATTACAGTGGAACTGAAGAAGGAGGAGGAATGTGAGAGCTAC

ACCGTCCGAGACCTCCTGGTCACCAACACCAGGGAGAATAAGAGCCGG

CAGATCCGGCAGTTCCACTTCCATGGCTGGCCTGAAGTGGGCATCCCC

AGTGACGGAAAGGGCATGATCAGCATCATCGCCGCCGTGCAGAAGCAG

CAGCAGCAGTCAGGGAACCACCCCATCACCGTGCACTGCAGCGCCGGG

GCAGGAAGGACGGGGACCTTCTGTGCCCTGAGCACCGTCCTGGAGCGT

GTGAAAGCAGAGGGGATTTTGGATGTCTTCCAGACTGTCAAGAGCCTG
```

CGGCTACAGAGGCCACACATGGTCCAGACACTGGAACAGTATGAGTTC

TGCTACAAGGTGGTGCAGGAGTATATTGATGCATTCTCAGATTATGCC

AACTTCAAGTAAGCGGCAACAAGGGTCCGTGGACCAGGAGGATTGCCT

TTAATATTTTGTAATATTCTGTTTTGTTAATATACCCCAAATTGTGTA

TATATCTTATAACTGTTTTAGAAATTGGTACATAGGCTTCTATTACCT

ATTAGGTGGAAATTTTATATGTAAATGTGTTAGCACTGATAGTCCTTT

TTCCAATGTTTTATTGGGGAATTAAATAGTGTGATGTTTGGATTGATA

TCGTGAAATCCTCAGCCGAGAAATTGGGCTGGATTGTGCTTTGGTTAA

TACATCTTTCCCTAAAGAAGATAAACACAAAATCCATTCCAGGTAGCT

CGGCACCAACTAAGAAAAAAAGCACAAAGTTCTCAGAGCTCTCGAGGA

AAGTGGTTGTCCCCGTACCACCATGCACTGTAAATATCCCTCCCCTCT

CTCCCTGGTCCCCTCCCCCATCCCCACCACTGATATCATGGGGAGTAA

TAGGACCAGAGCGGTATCTCTGGCACCACACTAGGGACTATCAGGTAA

TAAAAGCTTTGACTCCCTGAAAAAAAAAAAAAAAAAA.

Homo sapiens protein tyrosine phosphatase, receptor type, A (PTPRA), transcript variant 2 (NCBI Accession NM_080840.2):

(SEQ ID NO: 2)
CTGCGGCGAGTGCGGCGCTGACAGAGACGCGCGCGCGCGCGATCGCGC

TCGGACCCCGGCCGCTGCCGCCATCACTGTCGCCCGCCCAGTCGCCCC

TCAGCCGCTTCCCCTCGCCATGGAGGCGAGGCCGCCGCCGCCGCCGCG

GGGCTCGGAGCCGCGGGCCGGGCGGCGGCCCTGAGGGCTAGTGGCGGC

CCGAAACGCCGCCGCGGAGCCGAGGCGGAGCCGCTGTCCTCGTCCCCA

GCGGTCCCGCCCAACGCCCGACTCTGTGACACAACTAAAAAAAAACAA

AGGTATTTATGGAATTCCACTGAGTGGTAATGGATGATGCAGTTCAAA

TAACTAAGGACACATGTTCAAAGAGCATAATTAACTTTTTAAAAGAAG

CTAATAAGCATGGATTCCTGGTTCATTCTTGTTCTGCTCGGCAGTGGT

CTGATATGTGTCAGTGCCAACAATGCTACCACAGTTGCACCTTCTGTA

GGAATTACAAGATTAATTAACTCATCAACGGCAGAACCAGTTAAAGAA

GAGGCCAAAACTTCAAATCCAACTTCTTCACTAACTTCTCTTTCTGTG

GCACCAACATTCAGCCCAAATATAACTCTGGGACCCACCTATTTAACC

ACTGTCAATTCTTCAGACTCTGACAATGGGACCACAAGAACAGCAAGC

ACCAATTCTATAGGCATTACAATTTCACCAAATGGAACGTGGCTTCCA

GATAACCAGTTCACGGATGCCAGAACAGAACCCTGGGAGGGGAATTCC

AGCACCGCAGCAACCACTCCAGAAACTTTCCCTCCTTCAGATGAGACA

CCAATTATTGCGGTGATGGTGGCCCTGTCCTCTCTGCTAGTGATCGTG

TTTATTATCATAGTTTTGTACATGTTAAGGTTTAAGAAATACAAGCAA

GCTGGGAGCCATTCCAATTCTTTCCGCTTATCCAACGGCCGCACTGAG

GATGTGGAGCCCCAGAGTGTGCCACTTCTGGCCAGATCCCCAAGCACC

AACAGGAAATACCCACCCCTGCCCGTGGACAAGCTGGAAGAGGAAATT

AACCGGAGAATGGCAGACGACAATAAGCTCTTCAGGGAGGAATTCAAC

GCTCTCCCTGCATGTCCTATCCAGGCCACCTGTGAGGCTGCTTCCAAG

GAGGAAAACAAGGAAAAAAATCGATATGTAAACATCTTGCCTTATGAC

CACTCTAGAGTCCACCTGACACCGGTTGAAGGGGTTCCAGATTCTGAT

TACATCAATGCTTCATTCATCAACGGCTACCAAGAAAAGAACAAATTC

ATTGCTGCACAAGGACCAAAAGAAGAAACGGTGAATGATTTCTGGCGG

ATGATCTGGGAACAAAACACAGCCACCATCGTCATGGTTACCAACCTG

AAGGAGAGAAAGGAGTGCAAGTGCGCCCAGTACTGGCCAGACCAAGGC

TGCTGGACCTATGGGAATATTCGGGTGTCTGTAGAGGATGTGACTGTC

CTGGTGGACTACACAGTACGGAAGTTCTGCATCCAGCAGGTGGGCGAC

ATGACCAACAGAAAGCCACAGCGCCTCATCACTCAGTTCCACTTTACC

AGCTGGCCAGACTTTGGGGTGCCTTTTACCCCGATCGGCATGCTCAAG

TTCCTCAAGAAGGTGAAGGCCTGTAACCCTCAGTATGCAGGGGCCATC

GTGGTCCACTGCAGTGCAGGTGTAGGGCGTACAGGTACCTTTGTCGTC

ATTGATGCCATGCTGGACATGATGCATACAGAACGGAAGGTGGACGTG

TATGGCTTTGTGAGCCGGATCCGGGCACAGCGCTGCCAGATGGTGCAA

ACCGATATGCAGTATGTCTTCATATACCAAGCCCTTCTGGAGCATTAT

CTCTATGGAGATACAGAACTGGAAGTGACCTCTCTAGAAACCCACCTG

CAGAAAATTTACAACAAAATCCCAGGGACCAGCAACAATGGATTAGAG

GAGGAGTTTAAGAAGTTAACATCAATCAAAATCCAGAATGACAAGATG

CGGACTGGAAACCTTCCAGCCAACATGAAGAAGAACCGTGTGTTTTACAG

ATCATTCCATATGAATTCAACAGAGTGATCATTCCAGTTAAGCGGGGC

GAAGAGAATACAGACTATGTGAACGCATCCTTTATTGATGGCTACCGG

CAGAAGGACTCCTATATCGCCAGCCAGGGCCCTCTTCTCCACACAATT

GAGGACTTCTGGCGAATGATCTGGGAGTGGAAATCCTGCTCTATCGTG

ATGCTAACAGAACTGGAGGAGAGAGGCCAGGAGAAGTGTGCCCAGTAC

TGGCCATCTGATGGACTGGTGTCCTATGGAGATATTACAGTGGAACTG

AAGAAGGAGGAGGAATGTGAGAGCTACACCGTCCGAGACCTCCTGGTC

ACCAACACCAGGGAGAATAAGAGCCGGCAGATCCGGCAGTTCCACTTC

CATGGCTGGCCTGAAGTGGGCATCCCCAGTGACGGAAAGGGCATGATC

AGCATCATCGCCGCCGTGCAGAAGCAGCAGCAGCAGTCAGGGAACCAC

CCCATCACCGTGCACTGCAGCGCCGGGGCAGGAAGGACGGGGACCTTC

TGTGCCCTGAGCACCGTCCTGGAGCGTGTGAAAGCAGAGGGGATTTTG

GATGTCTTCCAGACTGTCAAGAGCCTGCGGCTACAGAGGCCACACATG

GTCCAGACACTGGAACAGTATGAGTTCTGCTACAAGGTGGTGCAGGAG

TATATTGATGCATTCTCAGATTATGCCAACTTCAAGTAAGCGGCAACA

AGGGTCCGTGGACCAGGAGGATTGCCTTTAATATTTTGTAATATTCTG

TTTTGTTAATATACCCCAAATTGTGTATATATCTTATAACTGTTTTAG

AAATTGGTACATAGGCTTCTATTACCTATTAGGTGGAAATTTTATATG

TAAATGTGTTAGCACTGATAGTCCTTTTTCCAATGTTTTATTGGGGAA

TTAAATAGTGTGATGTTTGGATTGATATCGTGAAATCCTCAGCCGAGA

-continued
```
AATTGGGCTGGATTGTGCTTTGGTTAATACATCTTTCCCTAAAGAAGA

TAAACACAAAATCCATTCCAGGTAGCTCGGCACCAACTAAGAAAAAAA

GCACAAAGTTCTCAGAGCTCTCGAGGAAAGTGGTTGTCCCCGTACCAC

CATGCACTGTAAATATCCCTCCCCTCTCTCCCTGGTCCCCTCCCCCAT

CCCCACCACTGATATCATGGGGAGTAATAGGACCAGAGCGGTATCTCT

GGCACCACACTAGGGACTATCAGGTAATAAAAGCTTTGACTCCCTGAA

AAAAAAAAAAAAAAA.
```

Homo sapiens protein tyrosine phosphatase, receptor type, A (PTPRA), transcript variant 3 (NCBI Accession NM_080841.2):

(SEQ ID NO: 3)
```
GTGACACAACTAAAAAAAAACAAAGGTATTTATGGAATTCCACTGAGT

GGTAATGGATGATGCAGTTCAAATAACTAAGGACACATGTTCAAAGAG

CATAATTAACTTTTTAAAAGAAGCTAGACTTCTTCAGAAGCTTGCCAG

TTTTTCAAGCTGATTTCTCTCACTGGCAACTCTTCAGAGTGCTGTTCC

TACTCCACCCTCCCCTGGTGATAAGCATGGATTCCTGGTTCATTCTTG

TTCTGCTCGGCAGTGGTCTGATATGTGTCAGTGCCAACAATGCTACCA

CAGTTGCACCTTCTGTAGGAATTACAAGATTAATTAACTCATCAACGG

CAGAACCAGTTAAAGAAGAGGCCAAAACTTCAAATCCAACTTCTTCAC

TAACTTCTCTTTCTGTGGCACCAACATTCAGCCCAAATATAACTCTGG

GACCCACCTATTTAACCACTGTCAATTCTTCAGACTCTGACAATGGGA

CCACAAGAACAGCAAGCACCAATTCTATAGGCATTACAATTTCACCAA

ATGGAACGTGGCTTCCAGATAACCAGTTCACGGATGCCAGAACAGAAC

CCTGGGAGGGAATTCCAGCACCGCAGCAACCACTCCAGAAACTTTCC

CTCCTTCAGATGAGACACCAATTATTGCGGTGATGGTGGCCCTGTCCT

CTCTGCTAGTGATCGTGTTTATTATCATAGTTTTGTACATGTTAAGGT

TTAAGAAATACAAGCAAGCTGGGAGCCATTCCAATTCTTTCCGCTTAT

CCAACGGCCGCACTGAGGATGTGGAGCCCCAGAGTGTGCCACTTCTGG

CCAGATCCCCAAGCACCAACAGGAAATACCCACCCCTGCCCGTGGACA

AGCTGGAAGAGGAAATTAACCGGAGAATGGCAGACGACAATAAGCTCT

TCAGGGAGGAATTCAACGCTCTCCCTGCATGTCCTATCCAGGCCACCT

GTGAGGCTGCTTCCAAGGAGGAAAACAAGGAAAAAAATCGATATGTAA

ACATCTTGCCTTATGACCACTCTAGAGTCCACCTGACACCGGTTGAAG

GGGTTCCAGATTCTGATTACATCAATGCTTCATTCATCAACGGCTACC

AAGAAAAGAACAAATTCATTGCTGCACAAGGACCAAAAGAAGAAACGG

TGAATGATTTCTGGCGATGATCTGGGAACAAAACACAGCCACCATCG

TCATGGTTACCAACCTGAAGGAGAGAAAGGAGTGCAAGTGCGCCCAGT

ACTGGCCAGACCAAGGCTGCTGGACCTATGGGAATATTCGGGTGTCTG

TAGAGGATGTGACTGTCCTGGTGGACTACACAGTACGGAAGTTCTGCA

TCCAGCAGGTGGGCGACATGACCAACAGAAAGCCACAGCGCCTCATCA

CTCAGTTCCACTTTACCAGCTGGCCAGACTTTGGGGTGCCTTTTACCC

CGATCGGCATGCTCAAGTTCCTCAAGAAGGTGAAGGCCTGTAACCCTC

AGTATGCAGGGGCCATCGTGGTCCACTGCAGTGCAGGTGTAGGGCGTA

CAGGTACCTTTGTCGTCATTGATGCCATGCTGGACATGATGCATACAG

AACGGAAGGTGGACGTGTATGGCTTTGTGAGCCGGATCCGGGCACAGC

GCTGCCAGATGGTGCAAACCGATATGCAGTATGTCTTCATATACCAAG

CCCTTCTGGAGCATTATCTCTATGGAGATACAGAACTGGAAGTGACCT

CTCTAGAAACCCACCTGCAGAAAATTTACAACAAAATCCCAGGGACCA

GCAACAATGGATTAGAGGAGGAGTTTAAGAAGTTAACATCAATCAAAA

TCCAGAATGACAAGATGCGGACTGGAAACCTTCCAGCCAACATGAAGA

AGAACCGTGTTTTACAGATCATTCCATATGAATTCAACAGAGTGATCA

TTCCAGTTAAGCGGGGCGAAGAGAATACAGACTATGTGAACGCATCCT

TTATTGATGGCTACCGGCAGAAGGACTCCTATATCGCCAGCCAGGGCC

CTCTTCTCCACACAATTGAGGACTTCTGGCGAATGATCTGGGAGTGGA

AATCCTGCTCTATCGTGATGCTAACAGAACTGGAGGAGAGAGGCCAGG

AGAAGTGTGCCCAGTACTGGCCATCTGATGGACTGGTGTCCTATGGAG

ATATTACAGTGGAACTGAAGAAGGAGGAGGAATGTGAGAGCTACACCG

TCCGAGACCTCCTGGTCACCAACACCAGGGAGAATAAGAGCCGGCAGA

TCCGGCAGTTCCACTTCCATGGCTGGCCTGAAGTGGGCATCCCCAGTG

ACGGAAAGGGCATGATCAGCATCATCGCCGCCGTGCAGAAGCAGCAGC

AGCAGTCAGGGAACCACCCCATCACCGTGCACTGCAGCGCCGGGGCAG

GAAGGACGGGGACCTTCTGTGCCCTGAGCACCGTCCTGGAGCGTGTGA

AAGCAGAGGGGATTTTGGATGTCTTCCAGACTGTCAAGAGCCTGCGGC

TACAGAGGCCACACATGGTCCAGACACTGGAACAGTATGAGTTCTGCT

ACAAGGTGGTGCAGGAGTATATTGATGCATTCTCAGATTATGCCAACT

TCAAGTAAGCGGCAACAAGGGTCCGTGGACCAGGAGGATTGCCTTTAA

TATTTTGTAATATTCTGTTTTGTTAATATACCCCAAATTGTGTATATA

TCTTATAACTGTTTTAGAAATTGGTACATAGGCTTCTATTACCTATTA

GGTGGAAATTTTATATGTAAATGTGTTAGCACTGATAGTCCTTTTTCC

AATGTTTTATTGGGGAATTAAATAGTGTGATGTTTGGATTGATATCGT

GAAATCCTCAGCCGAGAAATTGGGCTGGATTGTGCTTTGGTTAATACA

TCTTTCCCTAAAGAAGATAAACACAAAATCCATTCCAGGTAGCTCGGC

ACCAACTAAGAAAAAAGCACAAAGTTCTCAGAGCTCTCGAGGAAAGT

GGTTGTCCCCGTACCACCATGCACTGTAAATATCCCTCCCCTCTCTCC

CTGGTCCCCTCCCCCATCCCCACCACTGATATCATGGGGAGTAATAGG

ACCAGAGCGGTATCTCTGGCACCACACTAGGGACTATCAGGTAATAAA

AGCTTTGACTCCCTGAAAAAAAAAAAAAAAAAAA.
``` morpholino oligo PMO:

(SEQ ID NO: 4)
5' GACATTAAGGAATGCCTTACCCACA 3' morpholino oligo PMO:

(SEQ ID NO: 5)
5' GTGTCTCATCTGAAATCAAGACAAC 3'

What is claimed is:

1. A method of inhibiting receptor-type tyrosine-protein phosphatase alpha (PTPRA) protein activity in a cell, the method comprising contacting a cell with an effective amount of a PTPRA antagonist thereby inhibiting PTPRA protein activity in said cell, wherein said cell is a fibroblast-like synoviocyte, and wherein said PTPRA antagonist is an anti-PTPRA inhibitory nucleic acid.

2. The method of claim 1, wherein said anti-PTPRA inhibitory nucleic acid has at least 90% sequence identity to at least 10 contiguous nucleotides of SEQ ID NO: 1, SEQ ID NO: 2, SEQ ID NO: 3 or a complementary sequence thereof.

3. The method of claim 1, wherein said anti-PTPRA inhibitory nucleic acid has at least 90% sequence identity to at least 10 contiguous nucleotides of SEQ ID NO: 1, or a complementary sequence thereof.

4. The method of claim 1, wherein said anti-PTPRA inhibitory nucleic acid has at least 90% sequence identity to at least 10 contiguous nucleotides of SEQ ID NO: 2 or a complementary sequence thereof.

5. The method of claim 1, wherein said anti-PTPRA inhibitory nucleic acid has at least 90% sequence identity to at least 10 contiguous nucleotides of SEQ ID NO: 3 or a complementary sequence thereof.

6. The method of claim 1, wherein said anti-PTPRA inhibitory nucleic acid is a morpholino nucleic acid.

7. The method of claim 6, wherein said morpholino nucleic acid is a single stranded antisense nucleic acid.

8. The method of claim 6, wherein said morpholino nucleic acid has the sequence of SEQ ID NO:4 or SEQ ID NO:5.

9. The method of claim 6, wherein said morpholino nucleic acid is a phosphoramidate morpholino nucleic acid.

10. The method of claim 6, wherein said morpholino nucleic acid is conjugated to a cell permeable moiety.

11. The method of claim 8, wherein said morpholino nucleic acid has the sequence of SEQ ID NO:4.

* * * * *

UNITED STATES PATENT AND TRADEMARK OFFICE
CERTIFICATE OF CORRECTION

PATENT NO. : 10,604,585 B2
APPLICATION NO. : 15/509829
DATED : March 31, 2020
INVENTOR(S) : Bottini et al.

Page 1 of 1

It is certified that error appears in the above-identified patent and that said Letters Patent is hereby corrected as shown below:

In the Specification

At Column 1, Lines 18-21, please delete "This invention was made with government support under AR47825, AI07055 and UL1TR000100 awarded by the National Institute of Health. The government has certain rights in the invention." and insert -- This invention was made with government support under AI070555, AR047825, and TR000100, awarded by the National Institutes of Health. The government has certain rights in the invention. --

Signed and Sealed this
Twentieth Day of January, 2026

John A. Squires
*Director of the United States Patent and Trademark Office*